United States Patent
Desai et al.

(10) Patent No.: US 8,007,998 B2
(45) Date of Patent: Aug. 30, 2011

(54) POLYMERIZED CONJUGATES FOR BIOLOGICAL APPLICATIONS

(75) Inventors: Surbhi Desai, Rockford, IL (US); Michael Stanaitis, Love Park, IL (US); Ramesh Ganapathy, Love Park, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 0 days.

(21) Appl. No.: 12/671,407

(22) PCT Filed: Oct. 21, 2008

(86) PCT No.: PCT/US2008/080640
§ 371 (c)(1),
(2), (4) Date: Jan. 29, 2010

(87) PCT Pub. No.: WO2009/055387
PCT Pub. Date: Apr. 30, 2009

(65) Prior Publication Data
US 2010/0203533 A1    Aug. 12, 2010

Related U.S. Application Data

(60) Provisional application No. 60/981,589, filed on Oct. 22, 2007, provisional application No. 61/045,163, filed on Apr. 15, 2008.

(51) Int. Cl.
*C12Q 1/28* (2006.01)
*C12N 9/96* (2006.01)
*C12N 9/02* (2006.01)

(52) U.S. Cl. ............. 435/4; 435/7.1; 435/28; 435/188; 435/7.9; 435/7.5

(58) Field of Classification Search .................. None
See application file for complete search history.

(56) References Cited

U.S. PATENT DOCUMENTS
4,256,833 A    3/1981  Ali et al.
(Continued)

FOREIGN PATENT DOCUMENTS
EP    0913691    5/1999
WO    03/104424    12/2003

OTHER PUBLICATIONS

Hoshino et al., "The effect of polymerization of horseradish peroxidase on the peroxidase activity in the presence of excess H2O2: a background for a homogeneous enzyme immunoassay," J. Biochem., 1987, vol. 102, No. 4, pp. 785-791.*
RDI Poly-HRP Detection Technology, 1997, pp. 23-27.*

(Continued)

*Primary Examiner* — Shafiqul Haq
*Assistant Examiner* — Galina Yakovleva
(74) *Attorney, Agent, or Firm* — Thompson Hine LLP

(57) ABSTRACT

Polymerized conjugates of at least two proteins that have increased sensitivity for detecting proteins in biological assays such as gels and blots, and methods of preparing the conjugates, and a protein assay detection kit using the conjugates. In one embodiment, proteins are polymerized by reacting a carbohydrate group on the protein that has been oxidized with an amine group.

15 Claims, 17 Drawing Sheets

U.S. PATENT DOCUMENTS

| | | | |
|---|---|---|---|
| 6,027,874 A * | 2/2000 | Cucurou et al. | 435/5 |
| 2007/0117153 A1 | 5/2007 | Bieniarz | |
| 2007/0212730 A1 | 9/2007 | Vepari | |

OTHER PUBLICATIONS

International Preliminary Report On Patentability dated Apr. 27, 2010.

Extended European Search Report, dated Jan. 10, 2011.

Dhawan, S. Design and construction of novel molecular conjugates for signal amplification (I): conjugation of multiple horseradish peroxidase molecules to immunoglobulin via primary amines on lysine peptide chains. *Peptides* 23 (2002) 2091-2098.

International Search Report and Written Opinion, Completed Dec. 15, 2008, Mailed Jan. 5, 2009.

\* cited by examiner

US 8,007,998 B2

POLYMERIZED CONJUGATES FOR BIOLOGICAL APPLICATIONS

This application claims priority from PCT/US2008/080640 filed Oct. 21, 2008, which claims priority to U.S. Patent Application Ser. Nos. 60/981,589, filed Oct. 22, 2007, and 61/045,163, filed Apr. 15, 2008, each of which is hereby incorporated by reference in its entirety.

Methods of producing and using polymerized cross-linked conjugates in biological applications are disclosed.

Biological detection assays depend on the sensitivity of the detection moiety. Conjugates such as streptavidin-horseradish peroxidase (HRP) have shown promise in detection assays. In an attempt to enhance sensitivity, polymerized conjugates containing detection moieties have been produced. For example, polymerized HRP (polyHRP), containing covalently linked HRP homopolymers, enhance detection sensitivity because it quantitatively provides a plurality of signal-generating enzymes bound to one analyte molecule. PolyHRP conjugates with a carrier such as dextran to provide a backbone, are known.

Methods of making polymerized conjugates without a carrier backbone, and methods of using such conjugates in applications, are described. Such applications include, but are not limited to, enzyme linked immunosorbent assays (ELISA), oligonucleotide hybridization, use as probes, microarrays, Northern, Southern, and Western blots, chromatin immunoprecipitation, immunoassays, high throughput screening, etc.

Figure 1:
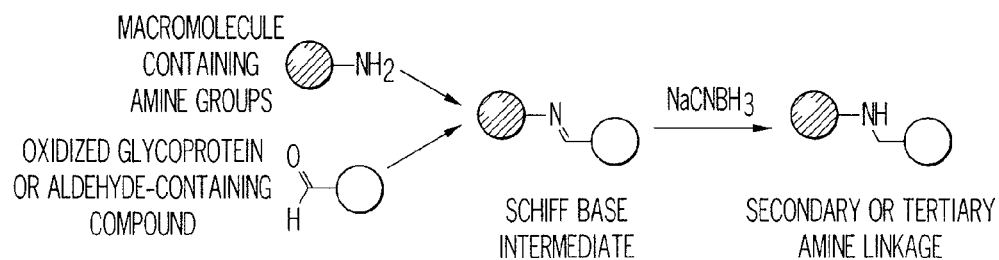
FIG. 1 shows a reaction scheme for reductive amination.

In one embodiment, a polymerized conjugate comprising at least protein 1 and protein 2 is formed by a reductive amination method, schematically represented in FIG. 1. The method a) oxidizes a carbohydrate, e.g. a hydroxyl group, on protein 1 and/or protein 2 to an aldehyde; then b) reacts the aldehyde produced with a primary amine group on protein 1 and/or protein 2 to form a Schiff base; and then c) reduces the Schiff base to form a stable, secondary amine. In one embodiment, protein 1 and protein 2 are both present during step a). In one embodiment, one of protein 1 or protein 2 is present during step a), and the other of protein 1 or protein 2 is added during step b) or any time after step a). In one embodiment, a carbohydrate group in, e.g., a glycoprotein, is a site for conjugation reactions. In embodiments, use of a carbohydrate group for conjugation leaves available amino acids that may be required for activity of the protein. In embodiments, a hydroxyl group of the carbohydrate is the reactive group.

In one embodiment, the carbohydrate in step a) is oxidized using sodium meta-periodate. Sodium meta-periodate is an oxidant that converts cis-glycol groups in carbohydrates to reactive aldehyde groups. Sodium meta-periodate cleaves bonds between adjacent carbon atoms that contain hydroxyl groups (cis-glycols), creating two aldehyde groups that are spontaneously reactive to amine- and hydrazide-activated compounds. Certain sugar groups are more susceptible to oxidative cleavage by periodate. Thus, the concentration of periodate, in a suitable buffer, may be altered in order to cleave particular sugars in a polysaccharide chain. As one example, treatment with 1 mM sodium meta-periodate oxidized only the bond between adjacent hydroxyls of sialic acid, a common terminal sugar residue in glycoprotein polysaccharides. As another example, treatment with greater than 10 mM sodium meta-periodate ensures oxidation of many sugar residues, including galactose and mannose. In one embodiment, sodium meta-periodate is present at a concentration in the range from about 25 mM to about 150 mM. In one embodiment, buffers that help maintain enzyme activity by maintaining the pH at or near physiological pH, e.g. about pH 6.8 to about pH 7.4, are used. In one embodiment, the buffer is phosphate buffered saline (PBS). In one embodiment, the pH of the reaction in step a) is about 7.2.

In step b), the aldehyde groups formed in step a) spontaneously form Schiff base bonds between aldehydes and amines. For example, primary amines exist in the side chain of lysine residues, which are generally abundant and readily accessible in proteins. In some embodiments, step b) further comprises increasing the pH of the reaction mixture of step a). In one embodiment, the pH is altered by dialyzing the reaction mixture against a buffer having the intended pH. Examples of dialysis buffers are known in the art and include buffers that do not contain primary amines, e.g. tris(hydroxymethyl)methylamine. For example, a borate buffer may be used. In one embodiment, the pH in step b) is increased to about pH 8.4. In one embodiment, the extent of the reaction of the aldehyde with the primary amine can be varied by varying the pH. For example, increasing the pH favors the reaction in step b). By varying the extent of the reaction in step b), the extent of conjugation between aldehyde and amine groups can be varied.

In step c), the Schiff base bonds that were formed in step b) are stabilized to secondary amines by a reduction reaction. In one embodiment, the reducing agent of step c) is sodium cyanoborohydride. In one embodiment, the reducing agent of step c) is sodium borohydride. In one embodiment, the reducing agent is present at a concentration in the range of about 5 mM to about 500 mM.

In one embodiment, the method results in a conjugate between protein 1 and protein 2 in the absence of a cross-linking agent. The conjugate can be used in any of the experimental protocols described below. Optionally, the conjugate also comprises conjugation of one molecule of protein 1 with another molecule of protein 1 and/or one molecule of protein 2 with another molecule of protein 2, thus forming a polymerized conjugate. In one embodiment, the conjugate has an approximate 1:1 ratio of protein 1 to protein 2. In one embodiment, the ratio of protein 1 to protein 2 varies from about 1:10 to about 10:1. The ratio of protein 1 to protein 2 in the resulting conjugate may be determined by various factors including the relative starting amounts of protein 1 and protein 2, the number of carbohydrate groups on protein 1 and/or protein 2, the number of amine groups on protein 1 and/or protein 2, the order of addition of protein 1 or protein 2, and/or the pH of step b).

In one embodiment, protein 1 and/or protein 2 contain at least one carbohydrate and/or amine group. In one embodiment, protein 1 and/or protein 2 has both carbohydrate and amine groups. In one embodiment, protein 1 and/or protein 2 is an indicator compound or a binding compound. In one embodiment, protein 1 and/or protein 2 can be modified or derivatized with agents that add functional groups prior to conjugation.

In one embodiment, an oxidizing agent, a reducing agent, and instructions for performing the method are provided in a kit. In one embodiment, the oxidizing agent is sodium metaperiodate. In one embodiment, the reducing agent is sodium cyanoborohydride. In one embodiment, the reducing agent is sodium borohydride. The kit may also contain materials for dialyzing the products of the method, and instructions for performing the method.

In one embodiment, a linker is present between at least one of protein 1 and protein 1, protein 2 and protein 2, or protein 1 and protein 2. In one embodiment, the linker is a protein. In one embodiment, the linker is bovine serum albumin. In one embodiment, the linker is an antibody or a portion thereof.

In one embodiment, an activated, polymerized indicator is formed. The activated, polymerized indicator can be conjugated to a molecular entity, such as a binding component. In one embodiment, the activated, polymerized indicator is horseradish peroxidase (polyHRP). In one embodiment, the polymerized, cross-linked conjugate is used to indicate its presence by generating or being able to generate a physically detectable compound in the sample assayed.

In one embodiment, the indicator functions as a label or marker and is detectable by standard techniques such as optical methods, e.g., spectrophotometry, fluorescence, luminescence, phosphorescence, etc.

One example of such an indicator is an enzyme, such as HRP, that catalyzes the production of a detectable product, such as a colored species, that is detectable by one or more of the physical methods described above. Other examples of indicator compounds include dyes, light-emitting compounds (e.g., fluorescent, luminescent, phosphorescent, etc.), metal-chelating substances including iminodiacetic acid, ethylenediaminetetraacetic acid (EDTA), diethylene triaminepentaacetic acid (DTPA), and desferrioxamine B, compounds labeled with a radioactive isotope, and/or compounds labeled with a heavy atom.

Examples of fluorescent compounds include fluorescein as fluorescein isothiocyanate, fluoresceinamine, 1-naphthol, 2-naphthol, eosin, erythrosin, morin, o-phenylenediamine, rhodamine, and 8-anilino-1-naphthalenesulfonic acid. Examples of detectable radioactive isotopes include isotopes of hydrogen (e.g., tritium ($^3$H)), carbon (e.g., $^{14}$C), phosphorus (e.g., $^{32}$P), sulfur (e.g., $^{35}$S), iodine (e.g., $^{131}$I), bismuth (e.g., $^{212}$B), yttrium (e.g., $^{90}$Y), technetium (e.g., $^{99m}$Tc), palladium (e.g., $^{109}$Pd) and samarium (e.g., $^{153}$Sm). Examples of heavy atoms include Mn, Fe, Co, Ni, Cu, Zn, Ga, In, Ag, Au, Hg, I, Bi, Y, La, Ce, Eu, and Gd.

One example of an indicator compound is a dye, which is any spectrophotometrically detectable molecule or derivative suitable for use in biological applications. Examples of dyes include visual dyes, phosphorescent dyes, fluorescent dyes, laser dyes, infrared dyes, and lanthanide chelates. Examples of visual dyes include soluble visual dyes such as solvent dyes, pigments, sulfur dyes, mordant dyes, and species such as fluorescein, rhodamine and derivatives (such as sulfur-rhodamine, rhodamine-hydride, and rhodamine hydrazide), oxazine dyes, cyanine dyes, and azol dyes. Specific examples of suitable dyes include, but are not limited to, Texas Red hydrazine, Congo Red, Trypan Blue, Lissamine Blue, Remazol Black, Remazol Brilliant Red, Rhodamine β Isothiocyanate, Cy5-Osu mono functional reactive dye, Reactive Orange 16, Uniblue A, etc.

A binding compound is capable of binding any other compound. In one embodiment, the binding compound has selective binding properties such that it functions as a detection probe, i.e., it binds to a compound of interest in a sample. Binding compounds include, but are not limited to, streptavidin, neutravidin, avidin, biotin, lectins, Protein A, Protein G, glycoproteins, peptides, hormones, receptors, antigens, drugs, antibodies and portions thereof, antigen binding fragments, RNA, DNA, and/or oligonucleotides.

In one embodiment, the binding compound is cross-linked to the indicator compound of the polymeric cross-linked conjugates. Cross-linking chemically joins two or more molecules by intermolecular forces, intramolecular forces, covalent bonds, and/or non covalent bonds such as ionic bonds, hydrogen bonds, and van der Waals attractions.

In one embodiment, cross-linking compounds contain one or more terminal groups with affinity for specific functional groups. A reactive terminus may be a molecule or functional group, termed a reactive group, that is reactive towards any other functional group, e.g. a target functional group. Cross-linking compounds may have the same functional groups on either terminus, such a cross-linking compound is a homobifunctional cross-linker. Cross-linking compounds may have different functional groups on either terminus, such a cross-linking compound is a heterobifunctional cross-linker.

Heterobifunctional cross-linkers have at least two different reactive groups that permit sequential conjugations with specific functional groups of, e.g., proteins. This embodiment minimizes undesirable polymerization or self-conjugation. Such functional and reactive group pairs include amine-carboxyl reactive with NHS-ester and amine/hydrazide via 1-ethyl-3-(3-dimethylaminopropyl)-carbodiimide (EDC) activation, amine-reactive photoreactive with NHS-ester and phenylazide, amine-sulfhydryl reactive with maleimide and NHS-ester, amine-sulfhydryl reactive with poly ethylene oxide (PEO)/poly ethylene glycol (PEG) spacers, maleimide and NHS-ester, carbohydrate reactive-photoreactive with hydrazide and phenyl azide, controlled sulfhydryl-carbohydrate reactive with hydrazide and maleimide, sulfydryl-carbonyl (aldehyde)/carboxyl reactive with maleimide and hydrazide, and sulfhydryl-hydroxyl reactive with maleimide and isocyanate. Table 1 lists representative cross-linker reactive groups and their corresponding target functional group.

TABLE 1

| Reactive Group | Target Functional Group |
| --- | --- |
| aryl azide | nonselective or primary amine |
| carbodiimide | amine/carboxyl |
| hydrazide | carbohydrate (oxidized) |
| hydroxymethyl Phosphine | amine |
| imidoester | amine |
| isocyanate | hydroxyl (non-aqueous) |
| carbonyl | hydrzine |
| maleimide | sulfhydryl |
| NHS-ester | amine |
| PFP-ester | amine |
| psoralen | thymine (photoreactive intercalator) |
| pyridyl disulfide | sulfhydryl |
| vinyl sulfone | sulfydryl, amine, hydroxyl |
| carbonyl | hydrazine |

Examples of heterobifunctional cross-linkers include sulfosuccinimidyl 4-(N-maleimidomethyl)cyclo-hexane-1-carboxylate (sulfo-SMCC); N-(ε-maleimidocaproyloxy) sulfosuccinimide ester (sulfo-EMCS); N-(γ-maleimidobutyryloxy) sulfosuccinimide ester (sulfo-GMBS); N—(K-maleimidoundecanecanoyloxy) sulfosuccinimide ester (sulfo-KMUS); sulfosuccinimidyl 6-(3'-(2-pyridyldithio)-propionamido)hexanoate (sulfo-LC-SPDP); m-maleimidobenzoyl-N-hydroxysulfosuccinimide ester (sulfo-MBS); sulfosuccinimidyl (4-iodoacety)aminobenzoate (sulfo-SIAB); sulfosuccinimidyl 4-(p-maleimidophenyl)butyrate (sulfo-SMPB); sulfosuccinimidyl-6-(α-methyl-α-(2-pyridyldithio)toluamido)hexanoate (sulfo-LC-SMPT); (N-succinimidyl-4-vinylsulfonyl)benzoate (SVSB); N-succinimidyl iodoacetate or iodoacetic acid N-hydroxysuccinimide ester (SIA); (succinimidyl 6-(4-iodoacetyl) amino methyl-cyclo-hexane-1-carbonyl)amino hexanoate (SIACX); succinimidyl 6(6-(((iodoacetyl)amino hexanoyl) aminohexanoate)) (SIAXX); p-nitrophenyl iodoacetate (NPI); sulfosuccinimidyl-2-[p-azidosalicylamido]ethyl-1,3'-dithiopropionate (SASD); N-[g-maleimidobutyryloxy]succinimide ester (GMBS), each of which is commercially available (Pierce, Rockford Ill.). Non-sulfonated forms of the above heterobifunctional cross-linkers may also be used.

In one embodiment, the cross-linking compound binds both the indicator compound and the binding compound. The cross-linking compound can react with functional groups present on the indicator and binding compounds. In one embodiment, the indicator compound and/or the binding compound is modified to possess functional groups that can react with the cross-linking compound. In one embodiment, the indicator compound and/or the binding compound may be modified or derivatized with agents that add functional groups.

In one embodiment, an indicator compound and/or binding compound is modified with appropriate reagents to add at least one more functional group than is present on the unmodified compound. The result is an activated indicator and/or binding compound. The additional functional groups include, but are not limited to, alkanes, alkenes, amides, amines, imines, sulfhydryls, esters, alcohol, ketones, aldehydes, carboxyl, carbohydrate, hydroxyl, hydrazine, and/or thymine. In one embodiment, an activated compound, such as an indicator or binding compound, can react with another compound in the absence of a cross-linking agent.

Figure 2:
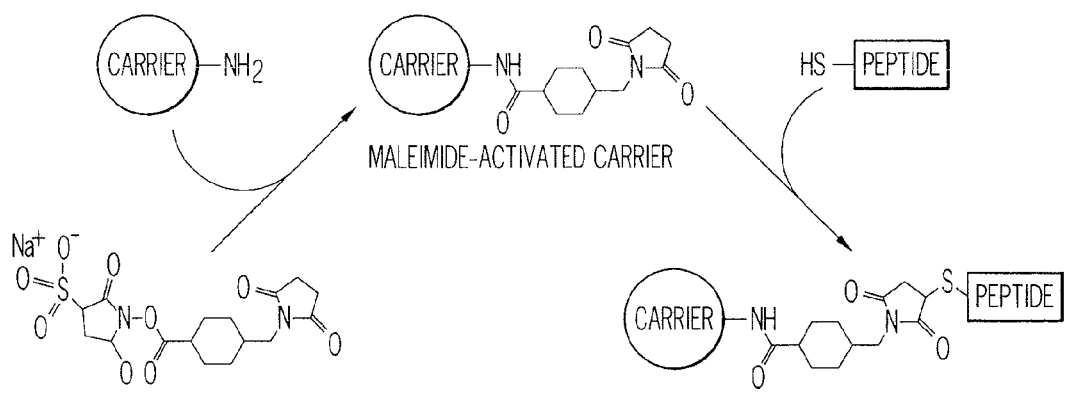
FIG. 2 shows the chemistry of a sulfosuccinimidyl 4-(N-maleimidomethyl)cyclo-hexane-1-carboxylate (sulfo-SMCC) cross-linker forming covalent bonds with an amine and sulfhydryl group.

In one embodiment, a maleimide group, for example, on a heterobifunctional cross-linker, reacts with a target sulfhydryl group to form a thioether bond, as shown in FIG. 2. HRP, an example of an indicator compound, does not contain free sulfhydryl groups. In one embodiment, 2-iminothiolane (Traut's Reagent) may be used to add a sulfhydryl group to HRP. Traut's Reagent reacts with primary amines (R—NH$_2$) on the HRP molecule to introduce sulfhydryl (—SH) groups while maintaining charge properties similar to the original amino group. Once added, sulfhydryl groups may be specifically targeted for reaction in a variety of labeling, cross-linking, and immobilization procedures. The functional group, examples of which are listed in Table 1, is selected based on its chemical reactivity with the reactive groups of the heterobifunctional cross-linker or an activated compound, to form covalent bonds.

Figure 3:
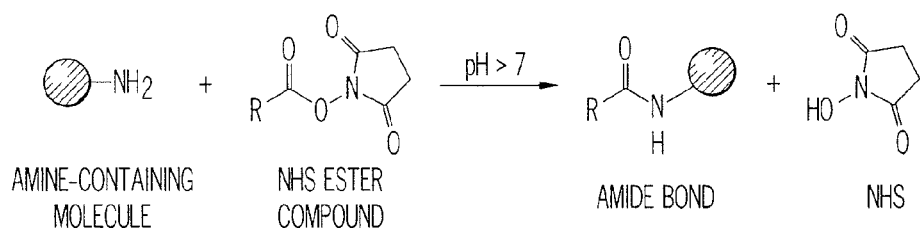
FIG. 3 shows an amine-containing molecule forming an amide bond with the N-hydroxysuccinimide (NHS) ester group.

In one embodiment, N-succinimidyl-S-acetylthioacetate (SATA) adds a sulfhydryl group to the indicator and/or binding compound. SATA reacts with primary amines to add protected sulfhydryls. SATA has an NHS ester group and a thioacetyl-protected sulfhydryl group and thus adds a thioacetyl-protected sulfhydryl group to the compound. When a free sulfhydryl is needed, a deprotection step is performed generating a free sulfhydryl containing compound that can be further conjugated. In general, a NHS ester reacts with primary amines, such as those on HRP, to form stable amide bonds, as shown schematically in FIG. 3.

Ligands that bind the binding compound generally have a high affinity for the binding compound and usually form a stable non-covalent bond between the ligand and the binding compound of the polymerized cross-linked conjugate. In one embodiment, the ligand/binding compound is biotin/streptavidin or biotin/avidin, i.e. the ligand is biotin and the binding compound is streptavidin or avidin. Biotin-streptavidin is a widely used binding pair because of the high binding affinity between biotin and streptavidin.

Streptavidin is a tetrameric protein, with each subunit binding one molecule of biotin with affinity similar to that of avidin. Streptavidin can be used in detection with biotin-labeled moieties such as oligonucleotides, primary antibodies, and secondary antibodies. Polymerized cross-linked conjugates prepared by the disclosed methods, using streptavidin or avidin as the binding compound, can be used as a template onto which any biotinylated moiety of interest may be attached. For example, biotinylated moieties include, but are not limited to, enzymes, hormones, solubilized receptor proteins, peptides, immunoglobulins, or other proteins of interest. In another embodiment, hapten/antibody systems may be used as a ligand/binding compound pair.

In one embodiment, polymerized HRP is conjugated to antibodies or other proteins of interest by derivatizing or modifying the proteins with a sulfhydryl adding agent, such as Traut's Reagent or SATA, and incubating with the maleimide-activated polymerized HRP for conjugation. The polymerized-protein conjugated complex is then purified, e.g., by dialysis or gel filtration.

In one embodiment, the polymerized-protein conjugated complex may be further modified. In one embodiment, an activated conjugated complex is reacted with an activated compound. In one embodiment, an activated, conjugated complex is reacted with an activated compound according to the scheme shown in FIG. 4, where the activated compound may be a component of the conjugated complex or an additional compound. For example, an activated poly HRP/streptavidin conjugated complex is reacted with activated poly HRP, as described in Example 10 and represented schematically in FIG. 5. Further modification of the conjugated complex permits modification and/or optimization of the ratio of the components in the conjugated complex.

In one embodiment, an amine containing compound is modified or derivatized with Traut's reagent or SATA to add a sulfhydryl group. The sulfhydryl containing compound may then be conjugated to a maleimide-activated polymerized HRP. Any protein bearing a free primary amino group can be conjugated according to the disclosed method, including enzymes, hormones, solubilized receptor proteins, peptides, immunoglobulins, etc. An oligonucleotide with an amino group can also be conjugated according to the disclosed method.

In one embodiment, a method of producing a polymerized conjugate complex, where the indicator compound is an enzyme and the binding compound is a protein, reacts an enzyme having an amino group with a heterobifunctional cross-linker, where the linker has a first group reactive with an amino group and a second group reactive with a sulfhydryl group, under conditions sufficient to permit the first group of the heterobifunctional linker to bond to the amino group of the enzyme, thereby forming an enzyme heterobifunctional linker conjugate; and reacts the enzyme-heterobifunctional linker conjugate with a protein having a sulfhydryl group reactive with the second group of the heterobifunctional linker, under conditions sufficient to permit the sulfhydryl group of the protein to bond to the second group of the heterobifunctional linker of the enzyme-heterobifunctional linker conjugate, to thereby form the enzyme-protein conjugate.

In one embodiment, an indicator compound is conjugated to a heterobifunctional cross-linker, which is then covalently attached to a binding compound. The binding compound is selected for its particular binding properties to certain compounds. In one embodiment, the conjugation method includes a heterobifunctional cross-linker with a first amine-reactive N-hydroxysuccinimide (NHS ester) group and a second sulfhydryl-reactive maleimide group. In one embodiment, the method further reacts an existing primary amine and introduces a protected amine group to the indicator compound. This ensures that a primary amine will be available for conjugation in later steps. The indicator compound containing the protected amine group is reacted with a heterobifunctional cross-linker, which introduces a maleimide group on the indicator molecule. The indicator molecule is reacted with a sulfhydryl group on the binding compound and conjugates the indicator compound to the sulfhydryl-activated binding compound.

In one embodiment, a method for making polymerized HRP-streptavidin conjugates with enhanced sensitivity is disclosed. The method may be used in assays including enzyme immunoassays (EIA), for cell and tissue staining, for blot immunostaining, etc.

Maleimide activated HRP was produced by reacting a mixture of reconstituted HRP (phosphate buffered saline (PBS), pH 7.2) and sulfo-succinimidyl-4-(N-maleimidomethyl)cyclohexane-1-carboxylate (sulfo-SMCC) for about 20 minutes to about 30 minutes at about 20° C. to about 22° C. (i.e., room temperature (RT)). The maleimide activated HRP was periodate-activated by treating with a 75 mM excess of sodium meta-periodate for about 10 minutes to about 20 minutes at RT and dialyzing against carbonate/bicarbonate buffer, pH 9.4. Sodium cyanoborohydride was then added to the mixture and allowed to react for about 90 minutes. After treatment with sodium cyanoborohydride, the mixture was dialyzed or desalted against PBS, pH 7.2, for about 90 minutes. After dialysis, maleimide-activated polymerized HRP was recovered.

A variety of heterobifunctional cross-linkers may be used to activate amines on the HRP. These heterobifunctional cross-linkers include sulfo-SMCC, sulfo-LC-SPDP, and/or SASD.

In one embodiment, to optimize the conjugation yield obtained from maleimide-activated HRP and Traut's Reagent activated streptavidin, different molar excesses of sulfo-SMCC were used for maleimide activation of the polyHRP. In one embodiment, up to a 10 molar excess was used.

In one embodiment, a sufficient amount of maleimide-activated HRP and derivatized streptavidin was incubated overnight at 4° C. to effect conjugation. The resulting polymerized HRP-streptavidin conjugate complex was used in desired applications, e.g., detection of specific proteins or antigens in immunoassays.

In one embodiment, the method controls the ratio of HRP/streptavidin by reacting HRP with a different molar excess of the cross-linking agent, for example, sulfo-SMCC. Increasing concentrations of sulfo-SMCC increase the maleimide groups attached to an HRP molecule. Increased numbers of maleimide groups allow increased streptavidin to be conjugated to an HRP molecule. Molar ratio of the HRP: streptavidin is defined as the moles of HRP divided by the moles of streptavidin in the final purified product. A lower HRP:streptavidin ratio is generally used in assays requiring lower sensitivity and in assays in which stearic hindrance due to molecule size is an issue. A higher HRP:streptavidin ratio is generally used in assays requiring higher sensitivity, e.g., to detect molecules that are in low abundance and/or in samples of limited quantity. In a polymer where multiple HRP polymers are attached to multiple streptavidin molecules, the sensitivity will still be increased even if the ratio between the HRP and streptavidin is low.

In one embodiment, a method to control the extent of HRP polymerization is disclosed. HRP contains carbohydrate groups (i.e., hydroxyl groups). Treatment with an excess of oxidizing agents such as sodium meta-periodate oxidizes these hydroxyl groups. The resulting aldehyde groups are reactive towards amine groups, such as primary amine groups on lysine residues in HRP. The reaction of the aldehyde and amine forms an imide bond resulting in homopolymerization of HRP. In one embodiment, a 75 molar excess of sodium meta-periodate treatment results in extensive homopolymerization. Lower concentrations of sodium meta-periodate result in less HRP polymerization. In embodiments, the cross-linking agent is selected to affect an extent of HRP polymerization.

In one embodiment, an activated polymerized HRP is in a form ready for use in assays. In one embodiment, the components and/or materials for use of the polymerized cross-linked conjugate is in kit form. Kit components and materials may vary, depending upon the purpose. In one embodiment, a kit may contain a polymerized reporter molecule, a heterobifunctional cross-linker, and a binding compound. In one embodiment, a kit may contain a polymerized reporter molecule, a homobifunctional cross-linker, and a binding compound. Components such as buffers, functional group modifiers, instructions, standards, and controls may be included.

In one embodiment, the molecular weight (MW) of the polymerized cross-linked conjugate is greater than about 140 kiloDaltons (KDa). In one embodiment, the MW of the polymerized cross-linked conjugate ranges from about 200 kDa to about 420 kDa.

In one embodiment, an ELISA method uses a polyHRP cross-linked conjugate with at least one biotinylated detection antibody having specificity for a particular antigen. A sample, containing an unknown amount of antigen or capable of containing antigen, is immobilized on a solid support (e.g., a polystyrene microtiter plate). Immobilization may be either non-specific (e.g., surface adsorption) or specific (e.g., capture by another antibody specific to the same antigen, such as in a sandwich ELISA). After immobilization, the biotinylated detection antibody is added and binds to the antigen, if present, forming a complex. Polymerized HRP-streptavidin conjugate is then added, with streptavidin binding to the biotinylated detection antibody. Between each step the plate is washed with a mild detergent solution to remove any non-specifically bound proteins or antibodies. After the final wash step, the plate is developed by adding an HRP substrate to produce a visible signal. Both chromogenic and fluorogenic HRP substrates can be used. The signal intensity indicates the quantity of antigen in the sample.

In one embodiment, a Western blot or immunoblot uses polyHRP-streptavidin cross-linked conjugate. Native or denatured proteins are separated by gel electrophoresis according to molecular weight (under denaturing conditions with sodium dodecyl sulfate (SDS)) or three-dimensional structure (under native, non-denaturing conditions). The proteins are then transferred to a membrane (typically nitrocellulose), where they are probed (detected) with biotynylated detection antibody specific to the target protein. The polymerized HRP-streptavidin conjugate is then added, with streptavidin binding to the biotynylated detection antibody. Between each step the membrane is washed with a mild detergent solution to remove any non-specifically bound proteins or antibodies. After the final wash step, the membrane is developed by adding an HRP substrate to produce a visible signal. Both chromogenic and fluorogenic HRP substrates can be used. The signal intensity indicates the quantity of antigen in the sample.

In one embodiment, the binding compound is an antibody and/or an antibody fragment. In one embodiment, the binding compound is a secondary antibody as known to a person having ordinary skill in the art, such as goat anti-mouse and goat anti-rabbit. In one embodiment, a polymerized conjugate has an antibody as the binding compound and HRP as the indicator compound.

In one embodiment, a linker is present between indicator compounds, between binding compounds, and/or between indicator and binding compounds. In one embodiment, the linker is a protein. Examples of suitable linker proteins include bovine serum albumin (BSA) and antibodies. In one embodiment, the linker protein is selected such that the linker has similar physical characteristics as the indicator compound, the binding compound, or both. For example, the linker may have the same or similar molecular weight as at least one of the indicator and the binding compounds. For example, BSA may be used as a linker in a conjugate where the binding compound is streptavidin because both BSA and streptavidin have similar molecular weights, as described in Example 11. In one embodiment, the linker may be, e.g., an IgG molecule, and the binding compound is an antibody. In one embodiment, the IgG linker molecule is a non-specific IgG antibody. In embodiments, the binding compound and the linker have similar molecular weights.

The method will be further appreciated with respect to the following non-limiting examples.

EXAMPLE 1

Maleimide activated HRP was prepared using 4×, 6×, 8×, and 10× molar excess of sulfo-SMCC. HRP (PBS, pH 7.2) was reconstituted at 50 mg/ml. HRP (25 mg) was modified with 4× sulfo-SMCC according to the following calculation: 25 mg/40,000 kDa×4×436=1.1 mg or 27.2 µl at 40 mg/ml in Milli Q H$_2$O (warmed to about 60° C.). 25 mg of HRP was modified with 6× sulfo-SMCC according to the following calculation: 25 mg/40,000 kDa×6×436=1.63 mg or 41 µl at 40 mg/ml in Milli Q H$_2$O (warmed to about 60° C.). 25 mg of HRP was modified with 8× sulfo-SMCC according to the following calculation: 25 mg/40,000 kDa×8×436=2.2 mg or 55 µl at 40 mg/ml in Milli Q H$_2$O (warmed to about 60° C.). 25 mg of HRP was modified with 10× sulfo-SMCC according to the following calculation: 25/40,000 kDa×10×436=2.7 mg or 67.5 µl at 40 mg/ml in Milli Q H$_2$O (warmed to about 60° C.).

The samples were incubated for thirty minutes at about 20° C. to about 22° C. (RT). Sulfo-SMCC activated HRP (2×25 mg) was periodate activated using a 75 molar excess of sodium meta-periodate according to the following calculation: 25 mg/40,000×75×214=10.03 mg (100.03 µl) at 100 mg/ml in Milli Q water. The reaction was continued for thirty minutes at RT. The sample was then dialyzed against carbonate/bicarbonate buffer, pH 9.4, with 4×500 ml changes and thirty minutes between each change.

Sodium cyanoborohydride (10 µl of 5 M) was added to the sample (0.75 ml after dialysis) and allowed to react for ninety minutes. The samples were dialyzed against 3×1 liter PBS.

EXAMPLE 2

It was calculated that 20 mg of the maleimide activated polyHRP from Example 1 was available for reacting with 2-iminothiolane derivatized streptavidin. Streptavidin (20 mg/ml in PBS) was derivatized with 2-iminothiolane (Traut's Reagent) dissolved at 10 mg/ml in Milli Q water as follows: streptavidin (15 mg) was modified with 6× Traut's Reagent according to the following calculation: 10 mg/60,000×6×138=0.207 mg (20.7 µl) at 10 mg/ml in Milli Q water. The reaction was carried out for forty minutes.

EXAMPLE 3

The maleimide activated polymerized HRP from Example 1 and the activated streptavidin from Example 2 were then conjugated. The concentration of maleimide-activated HRP recovered after dialysis was determined by determining the absorbance at 280 nm ($\lambda_{280}$) using 0.6 as the extinction coefficient for the polyHRP. The sample volume was about 0.5 ml and the concentration was 38 mg/ml. The amount of 2-iminothiolane-derivatized streptavidin required for conjugating to maleimide-activated polyHRP was determined using the following calculation: 19 mg/40,000×1/5×60,000=about 5.7 mg streptavidin. The samples were conjugated overnight at 4° C., and then purified by dialysis or gel filtration chromatography. The resulting polymerized HRP-streptavidin conjugate complex may be used in applications such as the detection of specific proteins or antigens in immunoassays.

EXAMPLE 4

HRP (50 mg/ml) was activated with 5×SATA according to the following calculation: 50 mg/40,000 kDa×5×231=1.44 mg (144 µl) at 10 mg/ml (2×72 µl). The activated sample was incubated for thirty minutes at RT. SATA-activated HRP was periodate activated using a 75 molar excess of sodium meta-periodate according to the following calculation: 50 mg/40,000 kDa×75×214=20.06 mg (200.6 µl) at 100 mg/ml. The reaction continued for sixty minutes at RT. The sample was then dialyzed against 4×1 liter carbonate/bicarbonate buffer for more than two hours. Sodium cyanoborohydride (30 μl of 5 M) was added and the sample was further reacted for sixty minutes. Ethanolamine (3 M), pH 9 (75 μl) was then added, and the sample was further reacted for fifteen minutes and then stored overnight at 4° C. The sample volume was made up to 2 ml. One ml was dialyzed against 2×500 ml PBS; one ml was purified by column chromatography.

EXAMPLE 5

Figure 6:
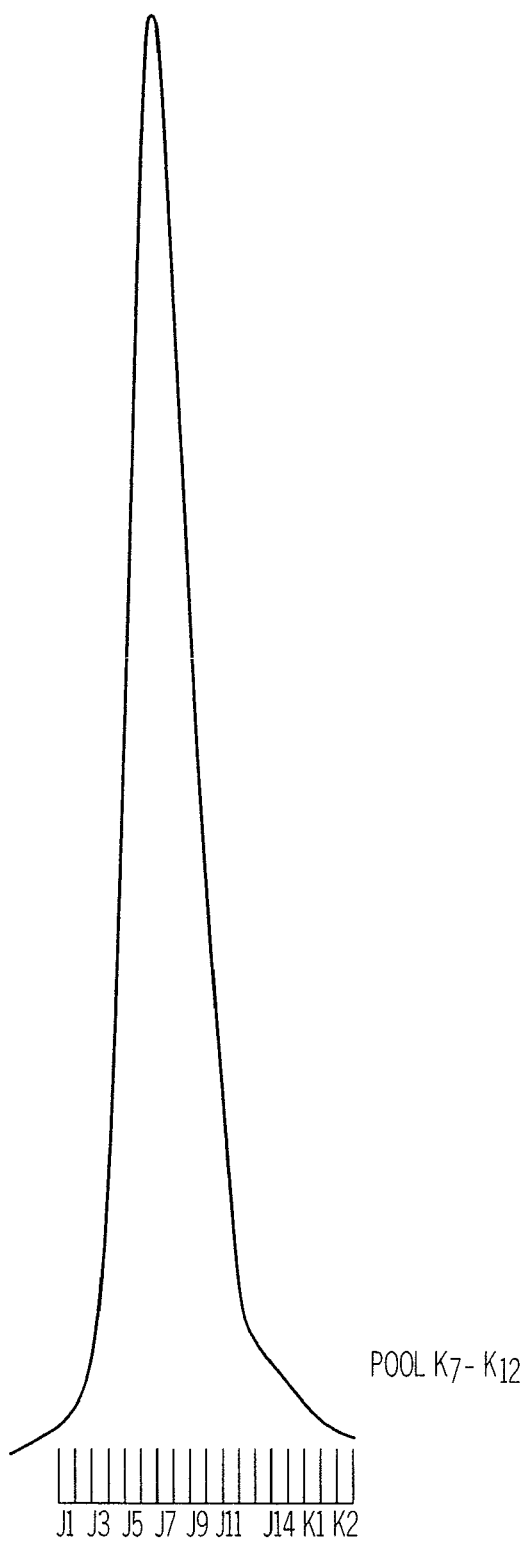
FIG. 6 shows a chromatogram of poly HRP-streptavidin conjugate after separation by size exclusion chromatography.

With reference to FIG. 6, the 5× poly HRP (monomer units) to maleimide activated sample was separated by fast protein liquid chromatography (FPLC). Peak 1 showed the polyHRP conjugated to maleimide activated streptavidin. Peak FPLC fractions were pooled and scanned. Predialyzed, dialyzed, and FPLC fractions were subjected to electrophoresis. Dialyzed polyHRP was conjugated to maleimide-activated streptavidin. Conjugation was performed at 6× polyHRP (monomer units). Protein concentration of dialyzed 6× polyHRP was calculated according to the following calculation: 1/60,000 kDa×6×40,000=4 mg (0.38 ml). PolyHRP (13 mg/ml) was then combined with 1 mg maleimide-activated streptavidin.

Dialyzed polyHRP was conjugated to maleimide-activated streptavidin. Conjugation was performed at 6× polyHRP (monomer units). Protein concentration of the polyHRP was determined at $\lambda_{280}$ with an extinction coefficient of 0.6 and the amount of SATA activated poly HRP required to couple with 1 mg of streptavidin was calculated as follows: 1/60,000 kDa×7.5×40,000=5 mg.

The maleimide-activated streptavidin and polyHRP were combined, then hydroxylamine HCl (HHCl) was added to initiate the maleimide-thiol reaction. The reaction continued for two hours. The reaction was quenched with sequential additions of each of 3 mM N-ethylmaleimide (NEM) and β-mercaptoethanol (BME), incubating for fifteen minutes after each addition. Table 2 lists the amounts of HHCl, NEM and BME added.

TABLE 2

| Vol. of MSA | Vol of PolyHRP | Total Vol Sample | Vol of HHCl (1M) | Vol. NEM (0.3M) | Vol BME (2 mM) |
|---|---|---|---|---|---|
| FPLC Peak #1/6X 0.1 ml (1 mg) | 1.33 ml | 1.43 ml | 71.5 μl | 15 μl | 6 μl |
| Dialyzed/6X 0.1 ml | 0.31 ml | 0.41 ml | 20.5 μl | 4.3 μl | 2 μl |
| Dialyzed/7.5X 0.1 ml | 0.39 ml | 0.49 ml | 25 μl | 5 μl | 2 μl |

Both FPLC and SDS-PAGE samples had a 6:1 ratio of mole HRP:mole streptavidin. In a functional assay using glutathione-coated plates, the activity of the FPLC purified polyHRP conjugate equaled the streptavidin HRP from Jackson ImmunoResearch Laboratory, Inc.

EXAMPLE 6

Samples from Example 1 (about 1 ml) were separated by FPLC on a high load 26/60 Superdex 75 preparatory grade column (flow rate 2 mL/min, degassed and sterile PBS buffer (0.1 M phosphate, 0.15 M NaCl, pH 7.2)). Fractions (1.75 mL) were collected. Fractions 14-111 and fractions K7-K12 were pooled. As shown in FIG. 6, the conjugate had a high, well-defined MW yielding an early eluting and sharp peak. The 4×, 6×, 8×, and 10× polyHRP conditions resulted in a HRP:streptavidin molar ratio of 2.6, 2.3, 1.8, and 2.0, respectively.

EXAMPLE 7

To functionally evaluate different sources of polyHRP-streptavidin, a functional assay was performed using gluthionine S-transferase (GST)-coated plates. Conjugates were normalized by the streptavidin HRP concentration.

GST was diluted with PBS to a concentration of 1.1 ng/ml, then serially diluted (1:3) in microwells of a plate and incubated for one hour at RT. The plate was then washed three times with PBS Tween (PBST). Biotinylated anti-GST at a dilution of 1:800 was added to each well and incubated for one hour at RT. The plate was washed three times with PBST. Streptavidin HRP (500 ng/ml or 50 ng/ml) was added, the plate was incubated for thirty minutes at RT, and then washed three times with PBST. The reaction was developed with 1 Step Turbo TMB™ (Pierce Biotechnology, Inc.) for five minutes, then quenched with 2 N sulfuric acid. Absorbance of solutions in the wells was determined at $\lambda_{450}$.

Figure 7:
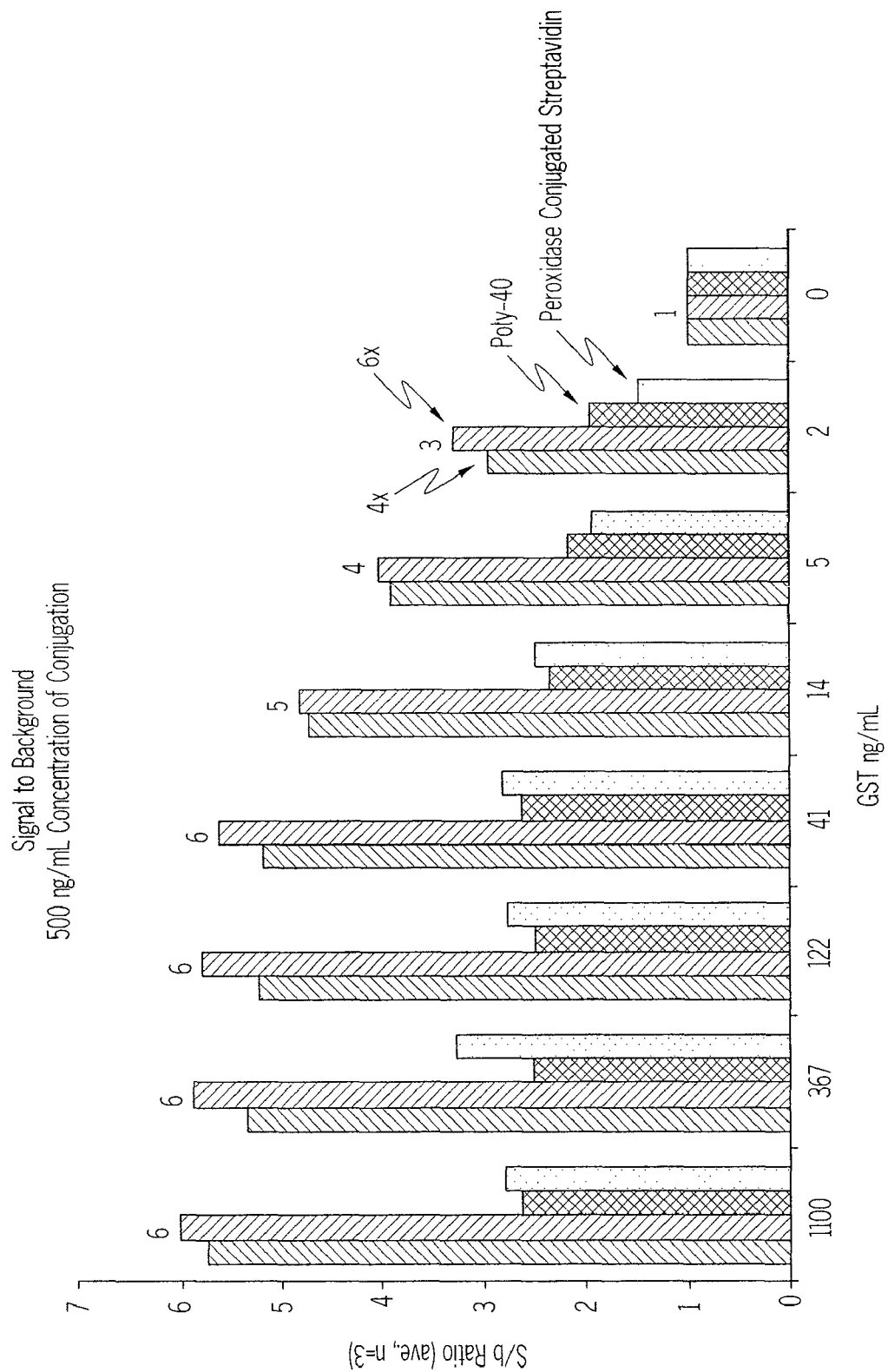
FIG. 7 shows results of an enzyme-linked immunosorbent assay (ELISA) comparing the signal to background ratio of different HRP-streptavidin conjugates.
Figure 8:
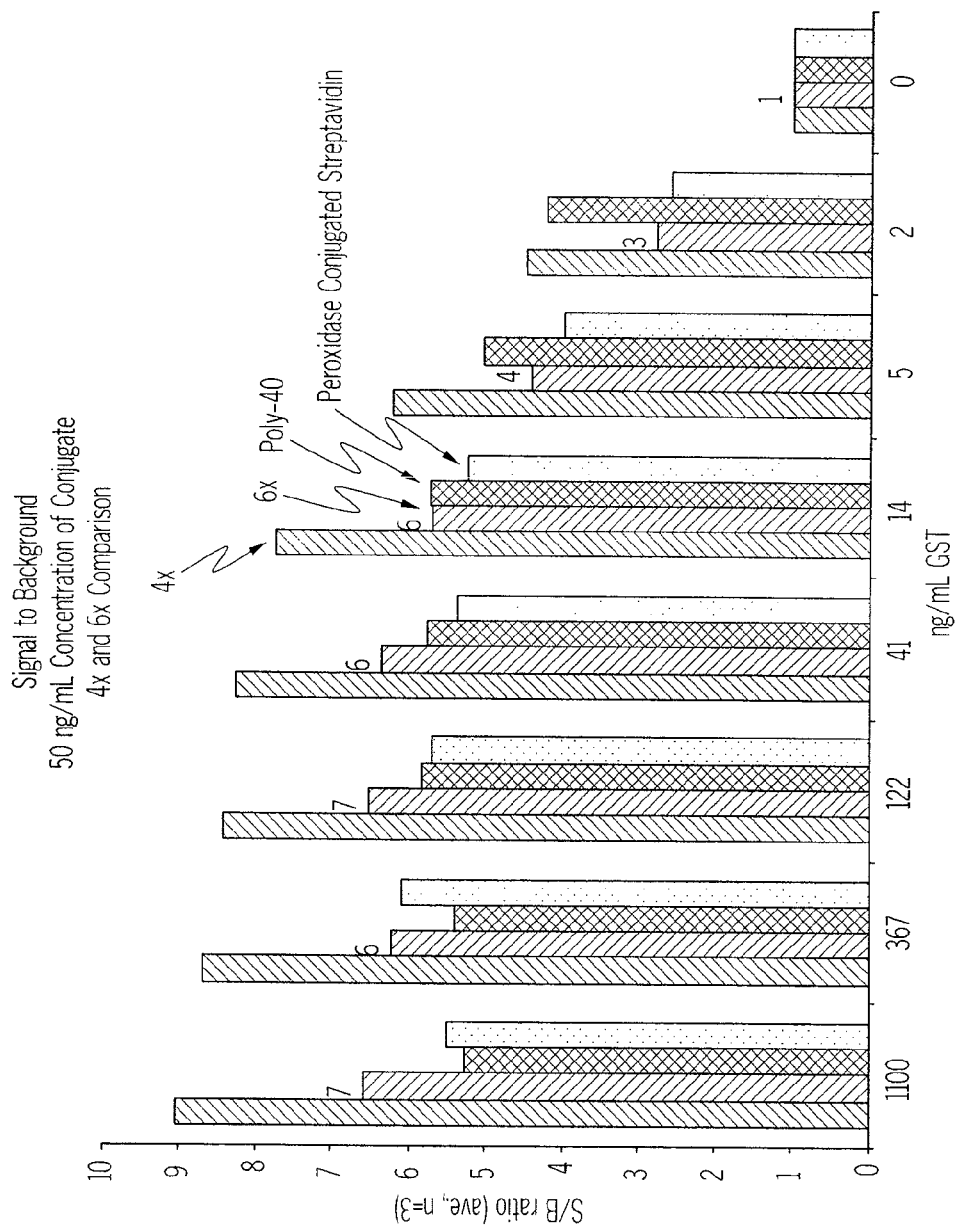
FIG. 8 shows results of an ELISA comparing the signal to background ratio of different HRP-streptavidin conjugates.
Figure 9:
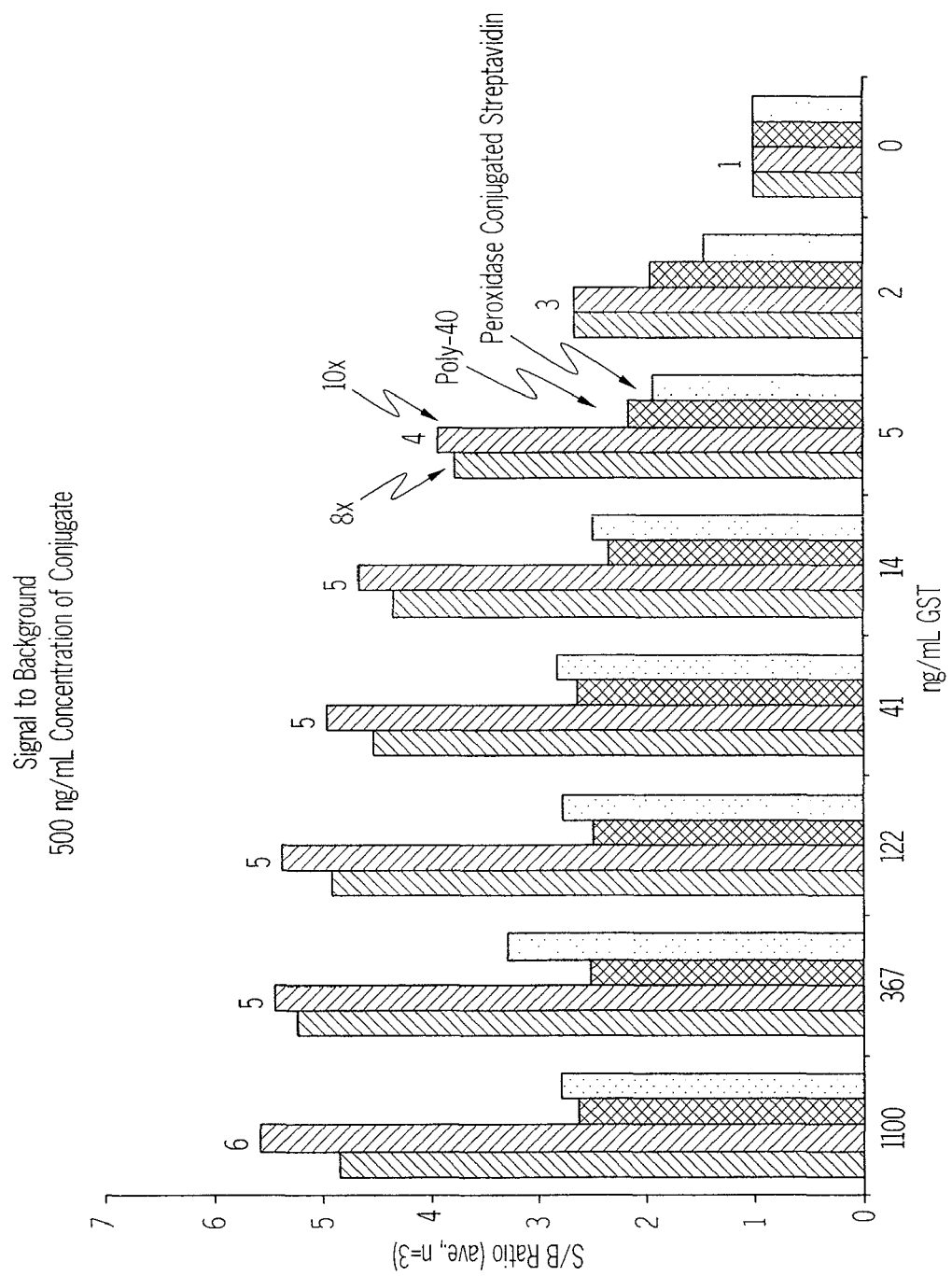
FIG. 9 shows results of an ELISA comparing the signal to background ratio of different HRP-streptavidin conjugates.
Figure 10:
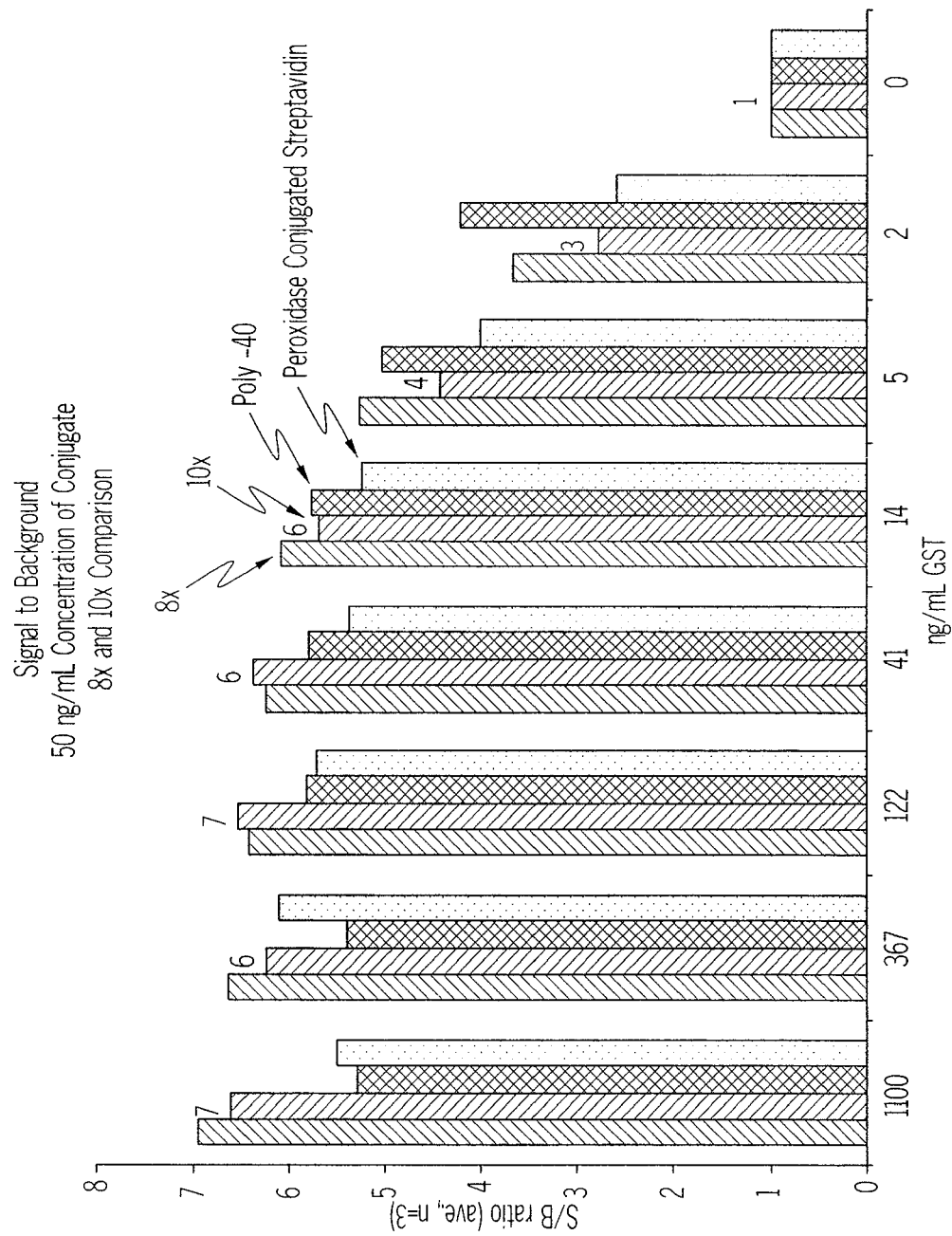
FIG. 10 shows results of an ELISA comparing the signal to background ratio of different HRP-streptavidin conjugates.

Results using 500 ng/ml of 4× and 6× polyHRP and 50 ng/ml of 4× and 6× polyHRP are shown in FIGS. 7 and 8. Results using 500 ng/ml of 8× and 10× polyHRP and 50 ng/ml of 8× and 10× polyHRP are shown in FIGS. 9 and 10, respectively. Molar ratio is defined as the moles of HRP divided by the moles of streptavidin in the final purified product. Therefore, the number of HRP molecules per 1 molecule of streptavidin in the 4×, 6×, 8×, and 10× conditions are 2.6, 2.3, 1.8, and 2.0, respectively. These data demonstrated the inventive conjugates had enhanced detection sensitivity and signal intensity as compared to commercially available products (e.g., Poly-40 (Research Diagnostics, Inc.), Peroxidase Conjugated Streptavidin (Jackson ImmunoResearch Laboratory, Inc.)).

EXAMPLE 8

The polymerized HRP-streptavidin conjugates were used in Western Blotting applications. Stock GST was diluted 1:5 in PBS, and this dilution was then serially diluted four times. These GST samples (10 μl) were loaded on 4-20% Precise gels and separated by electrophoresis at 100 V for 60 minutes. The separated proteins were transferred to nitrocellulose membranes at 40 v for 75 minutes. After the transfer, the membranes were blocked using Starting-Block blocking buffer in TBS. Biotinylated anti-GST antibody (1.1 mg/ml, 80 ng/ml final concentration) was diluted 1:2,500 in Starting-Block Blocking buffer. The membranes were incubated in 20 ml of this solution and incubated for thirty minutes at RT. The membranes were then washed five times with TBST, with five minute intervals between washes. Polymerized HRP-streptavidin conjugate samples (10 ng/ml), as used in Example 7, were prepared in 20 ml Starting-Block blocking buffer and added to the membranes. The membranes were incubated overnight at 4° C., washed five times with TBST, with five minute intervals between washes. The membranes were then incubated in 20 ml of ECL chemiluminescent reagent (Pierce Biotechnology, Inc.) for five minutes. Excess reagent was removed and the membranes were then developed by exposing to film (data not shown).

EXAMPLE 9

Figure 11:
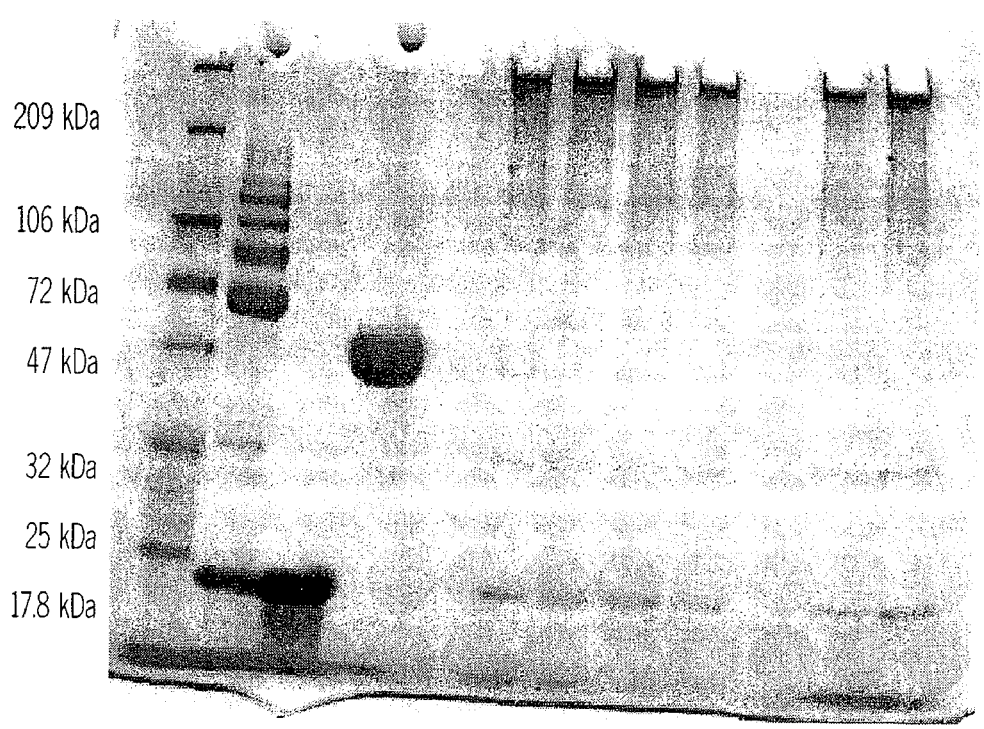
FIG. 11 shows separation of polyHRP-streptavidin conjugates formed according to one embodiment.
Figure 12:
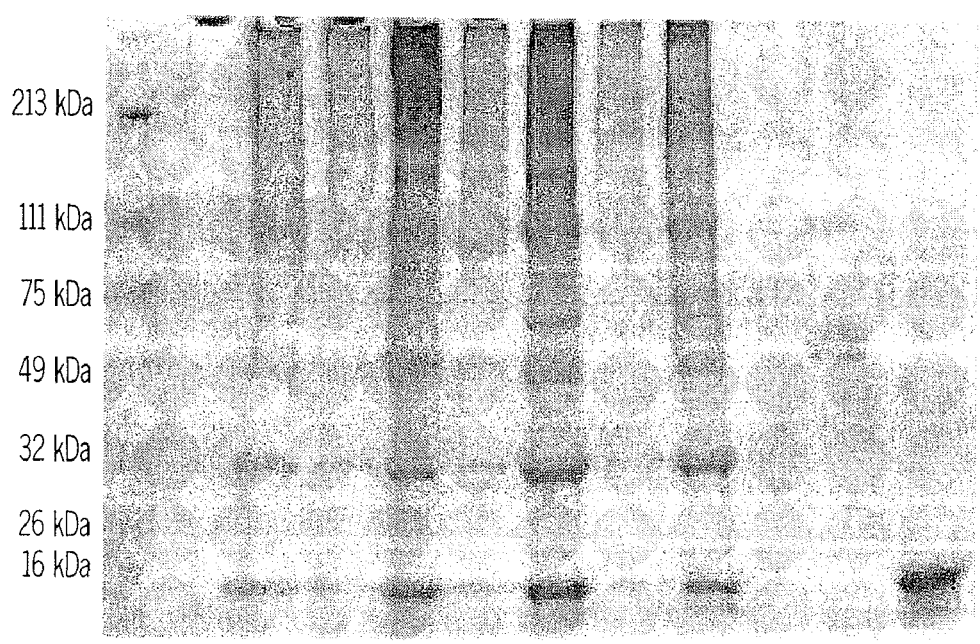
FIG. 12 shows separation of polyHRP-streptavidin conjugates formed according to one embodiment.

PolyHRP-streptavidin prepared using SATA-activated polyHRP and maleimide activated streptavidin, as shown in FIG. 11, and sulfo-SMCC-activated polyHRP and 2-iminothiolane activated streptavidin, as shown in FIG. 12, at different molar ratios (3×, 4×, 5×, 6×, 8×, 10×), were separated by SDS-PAGE to compare the extent of polymerization of HRP and the extent of HRP conjugated to streptavidin.

For results shown in FIG. 11, the samples were prepared by mixing 40 μl sample with 10 μl 5× sample buffer. The samples were heated for 5-10 minutes at 90° C. and then cooled to RT. Sample (10 μl) was applied per well to a 4%-12% TRIS-glycine gel as follows: lane 1: ChemiBlu Ranger marker; lane 2: HRP-streptavidin (2 mg/ml; Pierce #21127); lane 3: streptavidin (2 mg/ml); lane 4: HRP (2 mg/ml); lane 5: empty; lane 6: post-FPLC 4× polyHRP-streptavidin-conjugate; lane 7: post-FPLC 6× polyHRP-streptavidin-conjugate; lane 8: post-FPLC 8× polyHRP-streptavidin-conjugate; lane 9: post-FPLC 10× polyHRP-streptavidin-conjugate; lane 10: empty; lane 11: repeat conjugation of 6× polyHRP-streptavidin, post-FPLC; and lane 12: post-FPLC 8× polyHRP-streptavidin conjugate. The samples were subjected to electrophoresis for one hour at 100 v.

For results shown In FIG. 12, the samples were prepared by mixing 20 μl sample with 5 μl 5× sample buffer. The samples were heated for 5-10 minutes at 90° C. and then cooled to RT. Sample (10 μl) was applied per well to a 4%-12% TRIS-glycine gel as follows: lane 1: TriChromeRanger MW marker; lane 2: empty; lane 3: pre-FPLC 5× polyHRP-streptavidin; lane 4: 5× polyHRP-streptavidin post FPLC; lane 5: pre-FPLC 5× polyHRP-streptavidin dialyzed; lane 6: 5× polyHRP-streptavidin dialyzed post FPLC; lane 7: pre-FPLC 3× polyHRP-streptavidin; lane 8: 3× polyHRP-streptavidin post FPLC; lane 9: pre-FPLC 3× polyHRP-streptavidin dialyzed; lane 10: 3× polyHRP-streptavidin dialyzed post FPLC; lane 11: HRP (2.5 mg/ml); and lane 12: streptavidin (2 mg/ml).

FIGS. 11 and 12 show the result of the separations. HRP was polymerized and conjugated to streptavidin; the HRP (lane 4) and streptavidin (lane 3) were largely absent in the polyHRP-streptavidin samples in FIGS. 11 and 12 (lanes 6-9).

EXAMPLE 10

Figure 4:
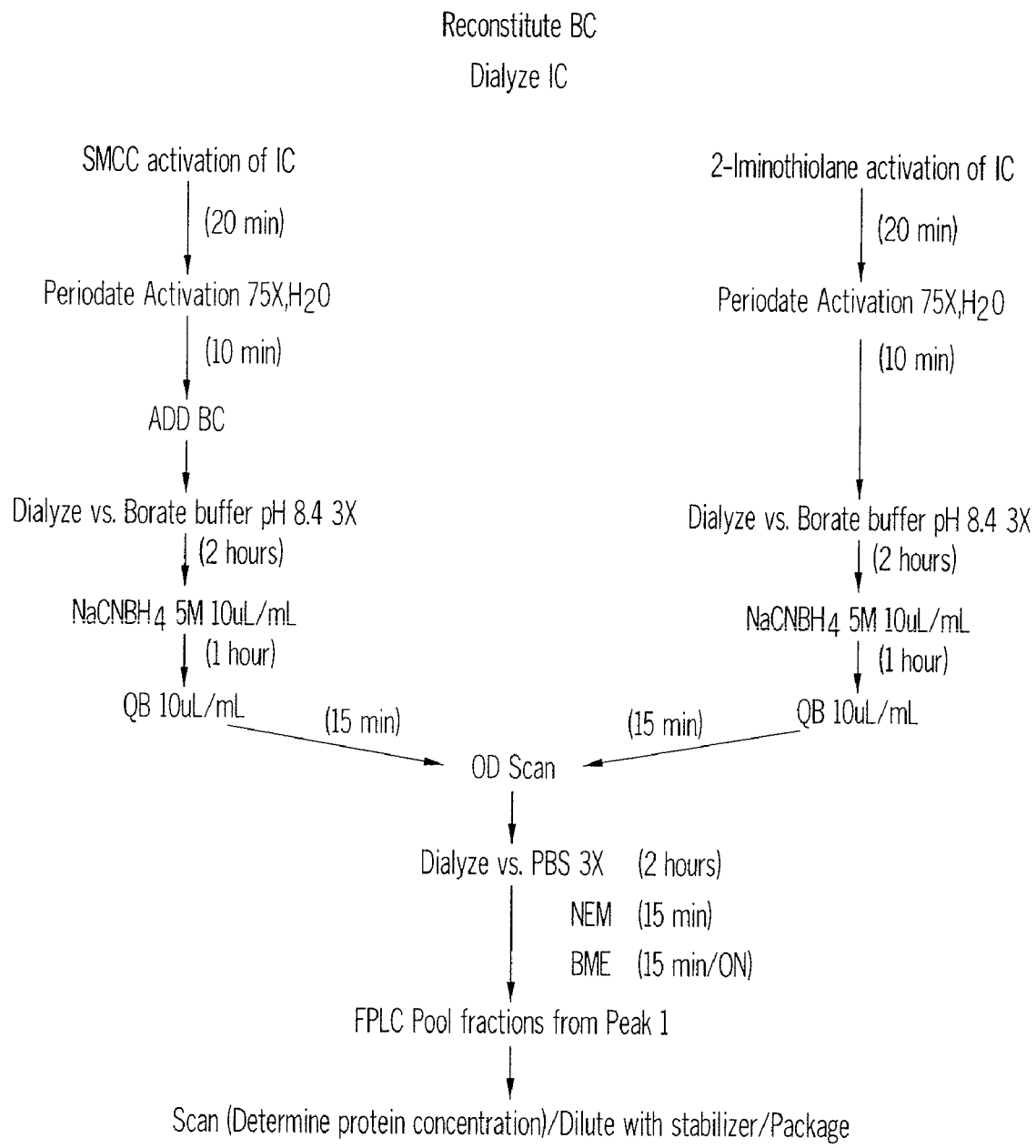
FIG. 4 is a flowchart for forming a polymerized conjugate according to one embodiment.
Figure 5:
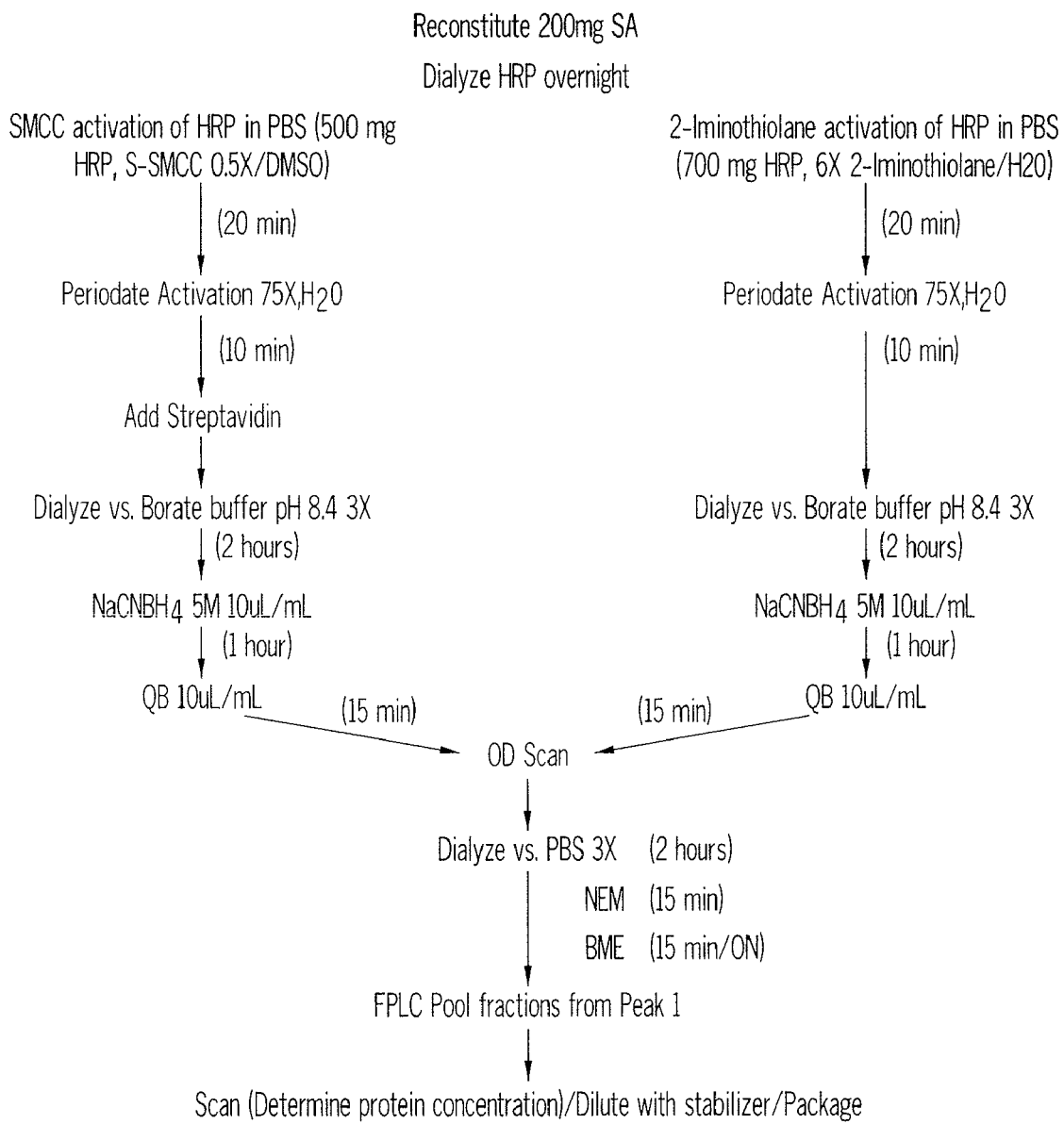
FIG. 5 is a flowchart for forming a polymerized horseradish peroxidase (poly HRP) streptavidin conjugate according to one embodiment.
Figure 13:
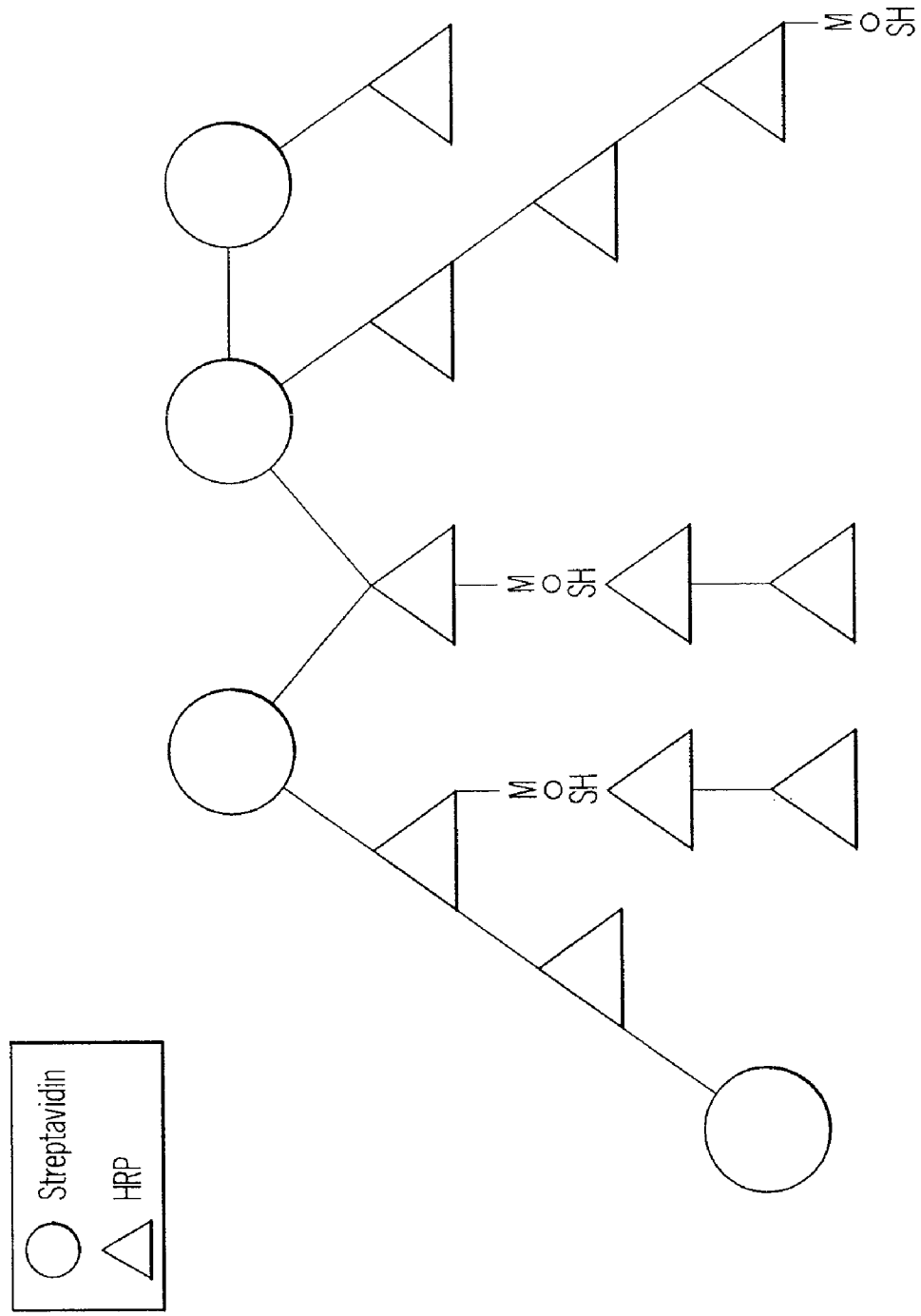
FIG. 13 is a schematic representation of a polymerized conjugate in one embodiment.

Streptavidin poly HRP was prepared, as shown schematically in FIG. 13, by the following method, as represented in flow chart form in FIG. 4. Streptavidin was reconstituted at 20 mg/ml and HRP at 50 mg/ml in 10 mM PBS. The reaction was performed with a ratio of 5 mg of HRP:1 mg of streptavidin.

HRP was dialyzed against two changes of 10 mM sodium phosphate buffer, pH 7.2. The protein concentration of streptavidin and HRP was determined by diluting each sample 1:50 and determining the absorbance at $\lambda_{280}$. A 0.5 molar excess of sulfo-SMCC, dissolved in DMSO at 10 mg/ml, was added to half the amount of the dialyzed HRP and allowed to react for 20 minutes. A 75 molar excess of sodium meta-periodate, dissolved in ultrapure water at 100 mg/ml, was added and allowed to react for 10 minutes. Streptavidin was then added.

To the remaining dialyzed HRP, a 6 molar excess of Traut's Reagent, dissolved in ultrapure water at 10 mg/ml, was added and allowed to react for 20 minutes. A 75 molar excess of sodium meta-periodate, dissolved in ultrapure water at 100 mg/ml, was then added and allowed to react for 10 minutes.

Both the maleimide-activated poly HRP/streptavidin sample and the Traut's Reagent activated poly HRP were injected into a 3-12 ml Slide-A-Lyzers® and dialyzed against 50 mM borate buffer at pH 8 for two hours. The samples were removed from the Slide-A-Lyzers® and 5 M sodium cyanoborohydride, prepared in 10 mM NaOH, was added and both samples were incubated for one hour. Quenching buffer, 3 M ethanolamine, was added to both samples and the samples were incubated for 15 minutes. The samples were then diluted 1:50 in 10 mM PBS and scanned from $\lambda_{500}$-$\lambda_{250}$.

The maleimide-activated poly HRP/streptavidin and the Traut's Reagent activated poly HRP were combined so that amounts which produced equal OD at $\lambda_{420}$ nm were mixed for each sample. The combined sample was dialyzed against two changes of 10 mM PBS. The unreacted sulfhydryl groups were quenched in the sample with 10 μl/ml N-ethyl maleimide (NEM), at 0.3 M in DMF, and incubated at RT for 15 minutes.

Figure 14:
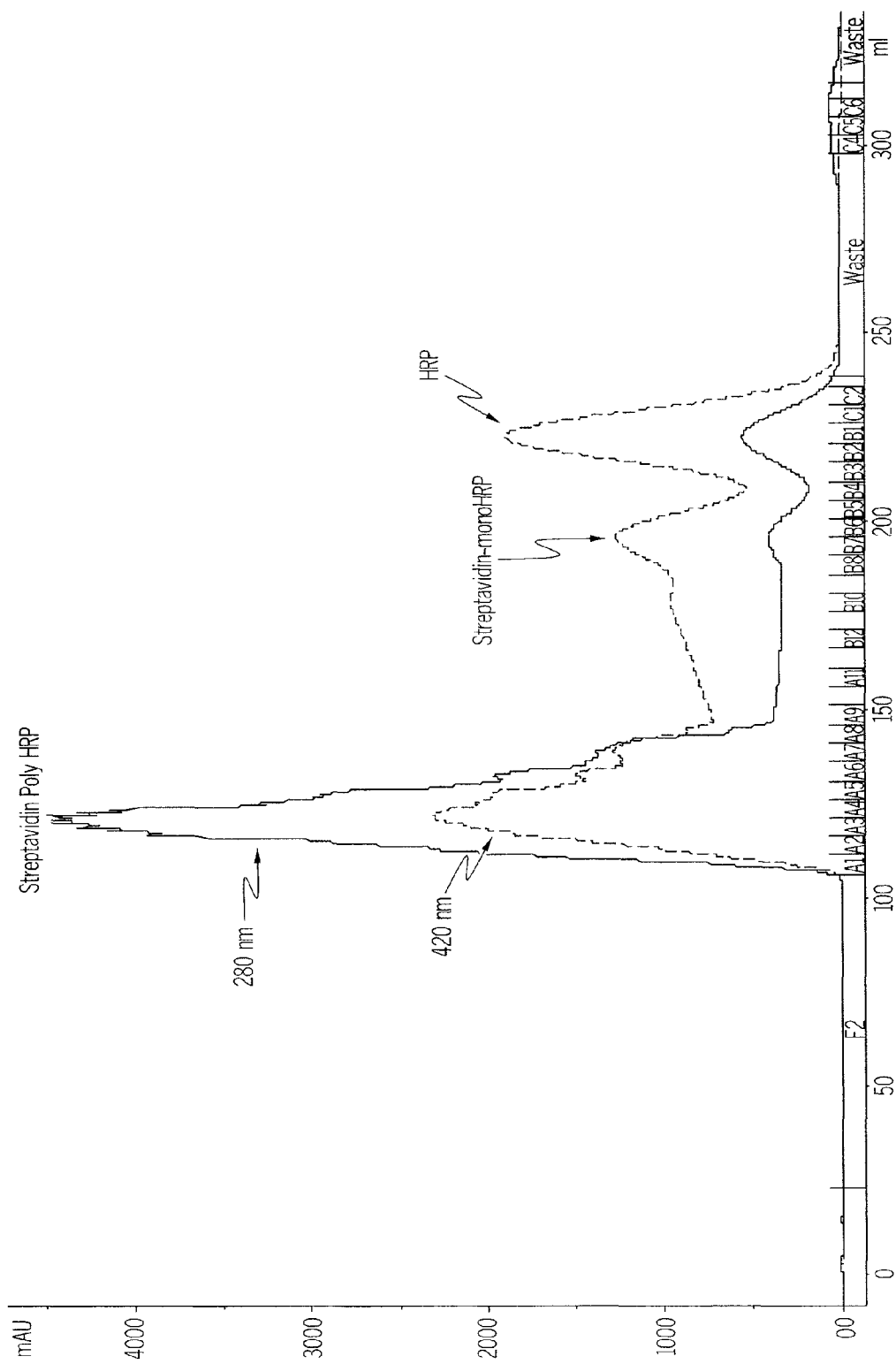
FIG. 14 shows chromatographs of products formed according to one embodiment.

The sample was purified using a Superdex 200 FPLC column and fractions from the first peak were pooled. The sample was scanned from $\lambda_{500}$ to $\lambda_{250}$ to determine the protein concentration and to evaluate the HRP to streptavidin ratio, with the scan at $\lambda_{280}$ and $\lambda_{420}$ shown in FIG. 14. The conjugate was diluted to 1 mg/ml with respect to protein concentration.

EXAMPLE 11

Figure 15:
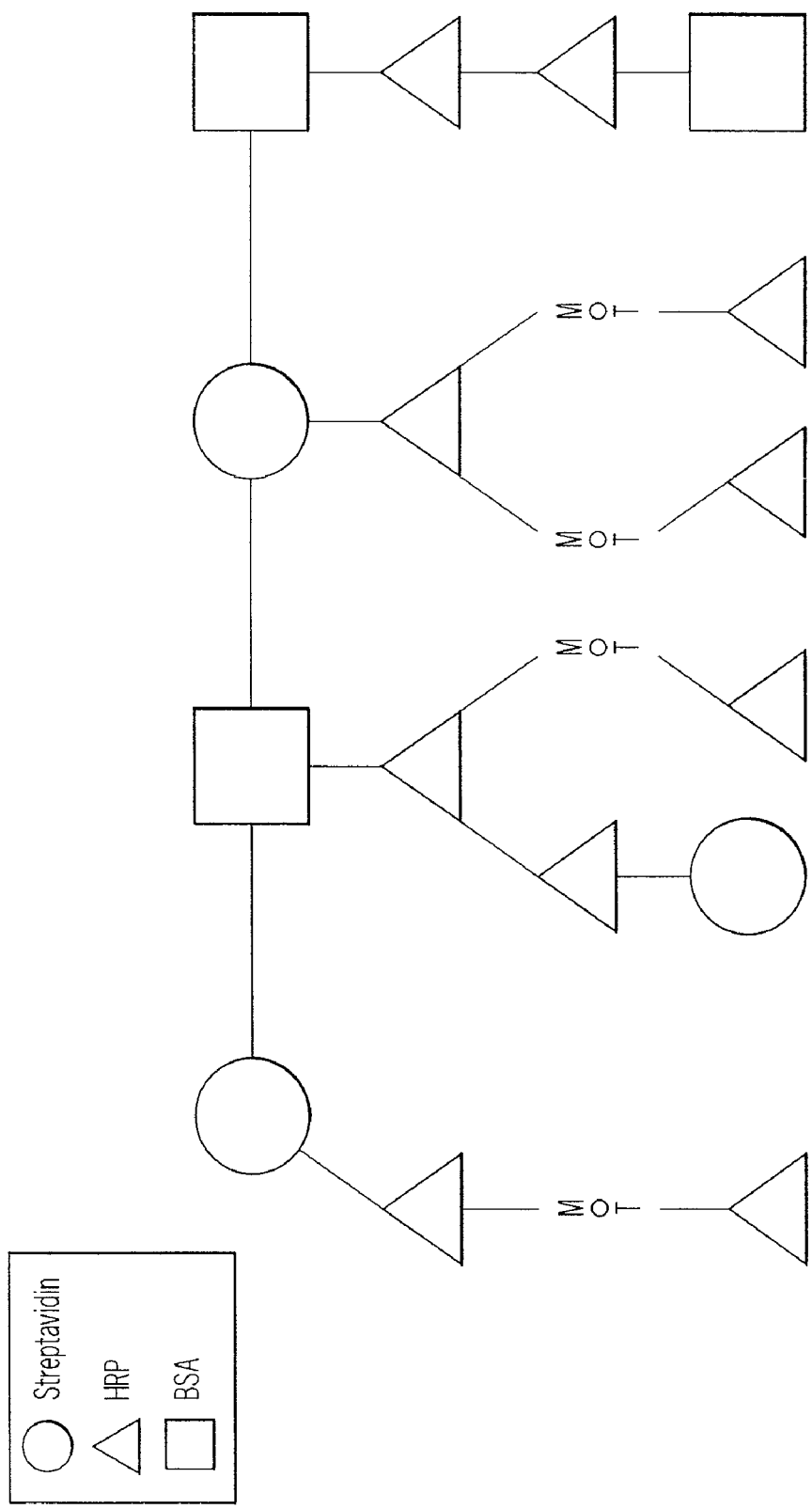
FIG. 15 is a schematic representation of a polymerized conjugate in one embodiment.

Streptavidin BSA poly HRP was prepared, as shown schematically in FIG. 15. Streptavidin was reconstituted at 20 mg/ml, BSA at 50 mg/ml, and HRP at 50 mg/ml in 10 mM PBS. The reaction was performed with a ratio of 5 mg of HRP:1 mg of streptavidin.

HRP was dialyzed against two changes of 10 mM sodium phosphate buffer, pH 7.2. The protein concentration of streptavidin, BSA, and HRP was determined by diluting each sample 1:50 and determining $\lambda_{280}$. A 0.5 molar excess of sulfo-SMCC, dissolved in DMSO at 10 mg/ml, was added to half the amount of the dialyzed HRP and allowed to react for 20 minutes. A 75 molar excess of sodium meta-periodate, dissolved in ultrapure water at 100 mg/ml, was added and allowed to react for 10 minutes. Streptavidin and BSA were then added at a 1:1 ratio.

To the remaining dialyzed HRP, a 6 molar excess of Traut's Reagent, dissolved in ultrapure water at 10 mg/ml, was added and allowed to react for 20 minutes. A 75 molar excess of sodium meta-periodate, dissolved in ultrapure water at 100 mg/ml, was then added and allowed to react for 10 minutes.

Both the maleimide-activated poly HRP/BSA/streptavidin sample and the Traut's Reagent activated polyHRP were injected into 3-12 ml Slide-A-Lyzers® and dialyzed against 50 mM borate buffer at pH 8 for two hours. The samples were removed from the Slide-A-Lyzers® and 5 M sodium cyanoborohydride, prepared in 10 mM NaOH, was added and both samples were incubated for one hour. Quenching buffer, 3 M ethanolamine, was added to both samples and the samples were incubated for 15 minutes. The samples were then diluted 1:50 in 10 mM PBS and scanned from $\lambda_{500}$-$\lambda_{250}$.

The maleimide-activated poly HRP/BSA/streptavidin and the Traut's Reagent activated poly HRP were combined so that amounts which produced equal OD at $\lambda_{420}$ nm were mixed for each sample. The combined sample was dialyzed against two changes of 10 mM PBS. The unreacted sulfhydryls were quenched in the sample with 10 μl/ml N-ethyl maleimide (NEM), at 0.3 M in DMF, and incubated at RT for 15 minutes.

The sample was purified using a Superdex 200 FPLC column and fractions from the first peak were pooled. The sample was scanned from $\lambda_{500}$ to $\lambda_{250}$ to determine the protein concentration and to evaluate the HRP to streptavidin ratio. The conjugate was diluted to 1 mg/ml with respect to protein concentration.

EXAMPLE 12

Streptavidin polyHRP (SPHRP) conjugate complexes, made using different methods, were compared in an ELISA. A goat anti-rabbit (GAR) coated plate was washed three times with 0.2 ml of PBS/0.05% Tween 20 (PBST). A 1:1 serial dilution of biotinylated rabbit anti-mouse antibody (BRAM; starting concentration 20 ng/ml) was made in PBST. A 0.1 ml sample of each different dilution of BRAM was added to wells of the plate. As a control, 0.1 ml of PBST was added to the control wells. The plate was incubated for one hour at RT and then washed three times with 0.2 ml PBST.

Figure 16:
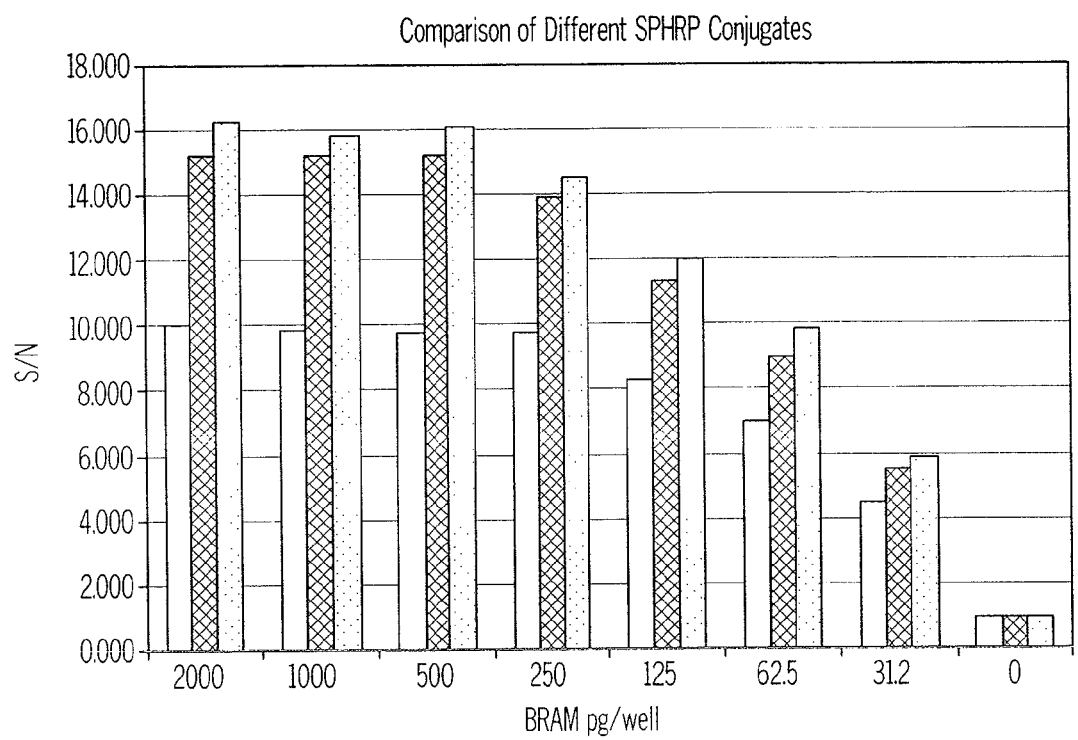
FIG. 16 shows ELISA results comparing streptavidin poly HRP conjugate complexes from various embodiments.

A 0.1 ml sample of three different poly HRP conjugates at 100 ng/ml was added to the plate wells in triplicate. The plate was incubated for one hour at RT and then washed three times with 0.2 ml PBST. A 0.1 ml aliquot of Ultra TMB substrate was added to each well of the plate and the plate was incubated for five minutes at RT. The reaction was stopped by adding 0.1 ml 2 N sulfuric acid and the plate was read at $\lambda_{450}$ using the Tecan Safire. The signal to noise ratio (S/N) at increasing biotin concentrations for streptavidin poly HRP conjugate formed as described in Example 10 using 10 mg of streptavidin and either 20 mg activated HRP (open bars) or 25 mg activated HRP (cross-hatched bars), and streptavidin BSA poly HRP conjugate formed as described in Example 11 (stippled bars) are shown in FIG. 16. These data demonstrated that the inventive conjugates had enhanced detection sensitivity and signal intensity.

EXAMPLE 13

A streptavidin BSA poly HRP (SBPHRP) conjugate complex was evaluated in an ELISA.

An interferon gamma (IFN γ) antibody coated plate was washed three times with 0.2 ml PBS/0.05% Tween 20 (PBST). A 1:1 serial dilution of IFN γ (starting concentration 1000 pg/ml) was made in PBST. A 0.1 ml aliquot of each IFN γ dilution was added to wells of the plate, with 0.1 ml PBST added to the control wells. The plate was incubated for one hour at RT and then washed three times with 0.2 ml PBST.

A 0.1 ml aliquot of biotinylated anti-IFN γ was added to each well in the plate and incubated. The plate was then washed four times with 0.2 ml PBST. A 0.1 ml sample of the streptavidin BSA poly HRP conjugate, as described in Example 11, at 100 ng/ml was added to the plate wells in triplicate and the plate was incubated for one hour at RT and then washed five times with 0.2 ml PBST.

Figure 17:
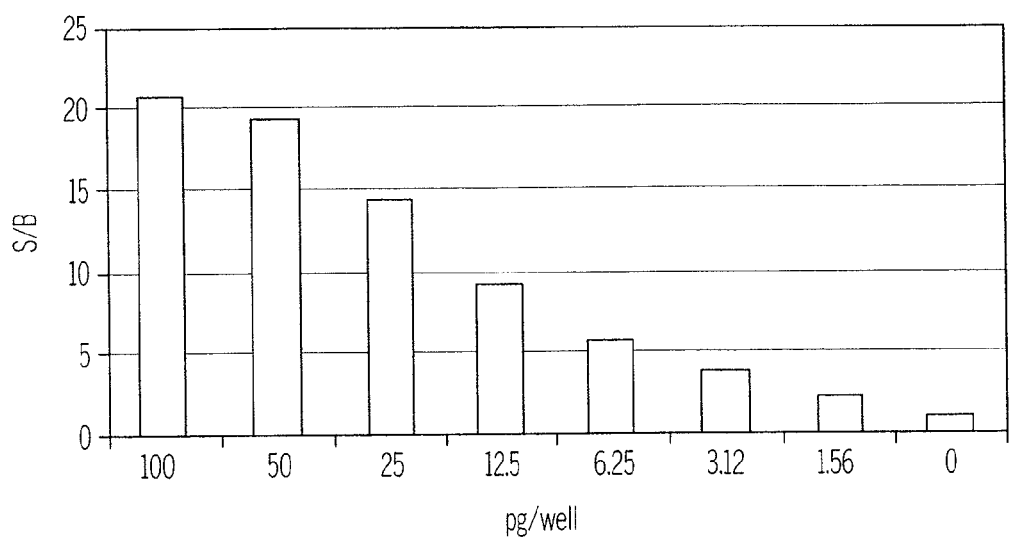
FIG. 17 shows ELISA results comparing streptavidin poly HRP conjugate complexes from various embodiments.

A 0.1 ml aliquot of Ultra TMB substrate was added to each well in the plate and the plate was incubated at RT for five minutes. The reaction was stopped by adding 0.1 ml 2N sulfuric acid and the plate was read at $\lambda_{450}$ using the Tecan Safire. The signal to background ratio (S/B) at increasing antibody concentrations for the streptavidin BSA poly HRP conjugate formed as described in Example 11 is shown in FIG. 17. These data demonstrated that the inventive conjugates had enhanced detection sensitivity and signal intensity.

EXAMPLE 14

A streptavidin BSA poly HRP (SBPHRP) conjugate complex was compared to a poly HRP complex in an ELISA.

A glutathione coated plate was washed three times with 0.2 ml PBS/0.05% Tween 20 (PBST). A 1:5 serial dilution of GST (starting concentration 1000 ng/ml) was made in PBST. A 0.1 ml sample of each GST dilution was added to wells of the plate, with 0.1 ml PBST added to the control wells. The plate was incubated for one hour at RT and washed three times with 0.2 ml PBST.

A 0.1 ml aliquot of biotinylated anti-GST (0.2 mg/ml) was added to each well in the plate and the plate was washed four times with 0.2 ml PBST. A 0.1 ml sample of the different poly HRP conjugates at 100 ng/ml was added to the plate wells in triplicate and the plate was incubated for one hour at RT and then washed five times with 0.2 ml PBST.

Figure 18:
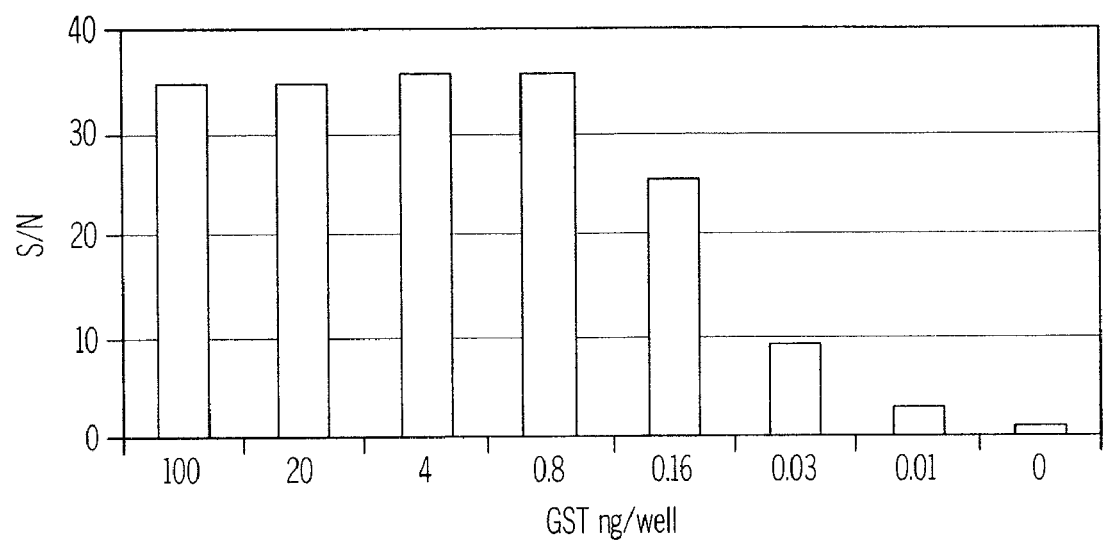
FIG. 18 shows ELISA results comparing streptavidin poly HRP conjugate complexes from various embodiments.

A 0.1 ml aliquot of Ultra TMB substrate was added to each well in the plate and the plate was incubated for five minutes at RT. The reaction was stopped by adding 0.1 ml 2N sulfuric acid and the plate was read at $\lambda_{450}$ using the Tecan Safire. The signal to noise ratio (S/N) at increasing GST concentrations for the streptavidin BSA poly HRP conjugate formed as described in Example 11 is shown in FIG. 18. These data demonstrated that the inventive conjugates had enhanced detection sensitivity and signal intensity.

EXAMPLE 15

A streptavidin poly HRP (SPHRP) conjugate complex was employed in a Western blot assay.

Figure 19:
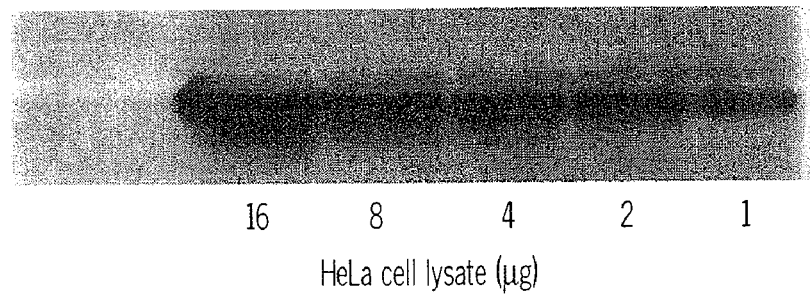
FIG. 19 shows Western blot results comparing streptavidin poly HRP conjugate complexes from various embodiments.

HeLa cell lysate (1.6 mg/ml) was serially diluted in Tris-glycine SDS sample buffer, heated 5 minutes at 95° C. and loaded onto Thermo Scientific Precise™ Protein Gels (4%-20%). After electrophoresis, the gels were washed in transfer buffer and transferred onto nitrocellulose membranes (0.2 μm). The membranes were blocked with StartingBlock (PBS) Blocking Buffer at room temperature for 2 hours. Before the experiment, 0.6 mg of anti-GAPDH was biotinylated using Thermo Scientific EZ-Link® Sulfo NHS-LC-Biotin. The biotinylated anti-GAPHDH was diluted to 1 μg/ml and 10 ml was added to each membrane and incubated overnight. The membranes were washed with PBS-Tween-20 and incubated for 1 hour at RT with a dilution of 1:4,000 of the streptavidin-HRP conjugate. After washing, Thermo Scientific Pierce ECL Substrate was added. The membranes were exposed to Thermo Scientific CL-Xposure Film for 5 seconds. As shown in FIG. 19, the Western blot showed excellent detection of nominal GAPDH levels in HeLa lysate using the streptavidin polyHRP conjugate.

EXAMPLE 16

Immunohistochemical (IHC) staining of cytokeratin 18 in human colon carcinoma was performed using a streptavidin polyHRP conjugate.

Formalin-fixed paraffin-embedded human colon carcinoma tissue (positive control tissue section, InnoGenex) was stained using Metal Enhanced DAB Substrate (Thermo Scientific ImmunoHisto Peroxidase Detection Kit). The tissue was subjected to heat-induced epitope retrieval using citrate buffer, followed by endogenous peroxidase quenching (Thermo Scientific Peroxidase Suppressor), and blocked. The tissue was incubated with rabbit anti-cytokeratin 18 (Abcam) at 18.6 μg/ml for 30 minutes at RT. For the negative control, another tissue slide was incubated with blocking buffer only. Tissues were thoroughly washed with 0.05% Tween-20 and incubated with biotinylated-goat anti-rabbit highly cross-adsorbed antibody at 1.46 μg/ml for 30 minutes at RT and washed. Tissues were then incubated with streptavidin poly-HRP at 4 μg/ml. The Metal Enhanced DAB Substrate working solution was added to the tissue according to the protocol and incubated for 5 minutes. All tissues were counterstained using a Harris-modified hematoxylin solution. The tissues were dehydrated and cover slip-mounted using the mounting medium provided in the kit. Images were acquired using a Nikon TE200 Microscope at a 20× magnification, using Spot RT-InSight camera.

Figure 20A:
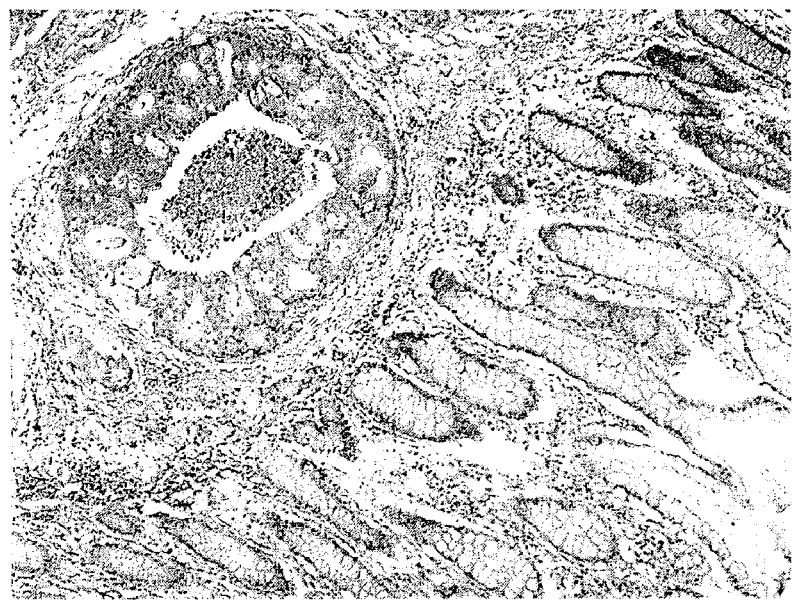
FIG. 20A shows the negative control of an immunohistochemical result.
Figure 20B:
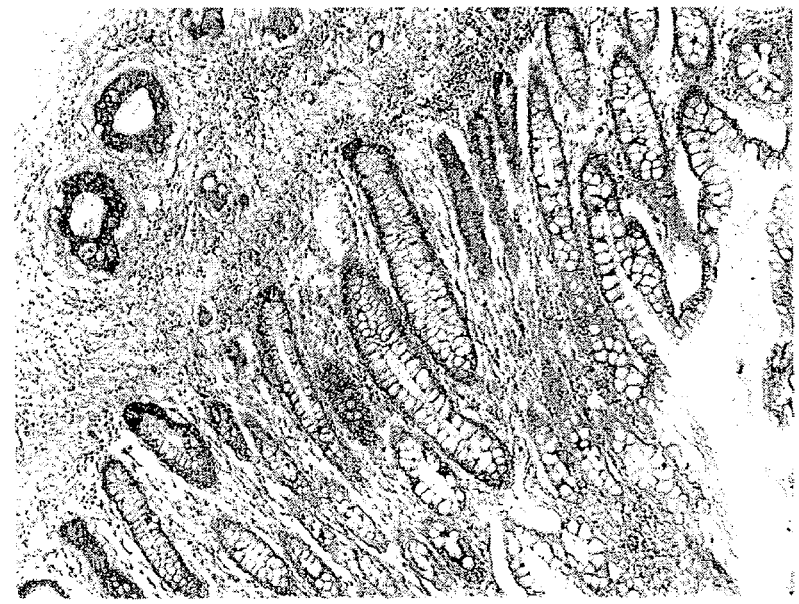
FIG. 20B shows immunohistochemical staining with streptavidin poly HRP.

Cytokeratin 18 was distinctively stained in brown in the basal membrane of the human colon carcinoma cells using the streptavidin poly HRP conjugate, as shown in FIG. 20B. The negative control sample, as shown in FIG. 20A, showed no brown staining within the tissue sample.

EXAMPLE 17

Figure 21:
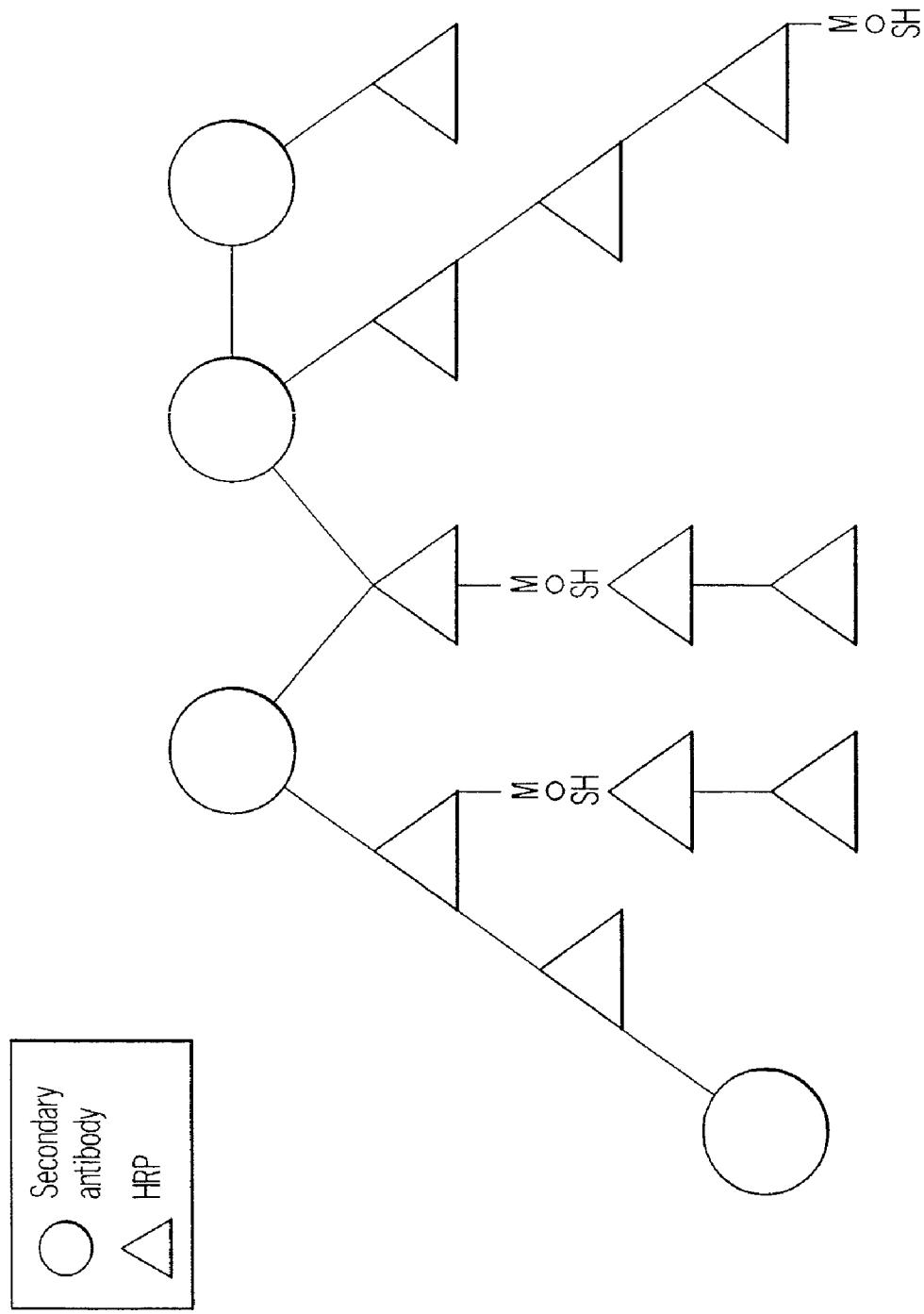
FIG. 21 is a schematic representation of a polymerized conjugate in one embodiment.

Secondary antibody poly HRP conjugate, as shown schematically in FIG. 21, at a ratio of 3.3 mg of HRP:1 mg of secondary antibody was prepared. The secondary antibody and HRP were reconstituted at 10 mg/ml and 50 mg/ml, respectively, in 10 mM PBS. The HRP was dialyzed against two changes of 10 mM sodium phosphate buffer, pH 7.2 followed by determining the protein concentration of the secondary antibody and HRP by diluting each sample 1:50 and determining the $\lambda_{280}$.

A 0.5 molar excess of sulfo-SMCC, dissolved in DMSO at 10 mg/ml, was added to half the amount of the dialyzed HRP, at a ratio of 1.1 mg HRP:1 mg of secondary antibody, and allowed to react for 20 minutes. A 75 molar excess of sodium meta-periodate, dissolved in ultrapure water at 100 mg/ml, was then added and allowed to react for 10 minutes, followed by the addition of the required amount of secondary antibody.

To the remaining dialyzed HRP, a six molar excess of Traut's Reagent dissolved in ultrapure water at 10 mg/ml was added to achieve a ratio of 2.2 mg HRP:1 mg secondary antibody, and allowed to react for 20 minutes. A 75 molar excess of sodium meta-periodate, dissolved in ultrapure water at 100 mg/ml, was then added and allowed to react for 10 minutes.

Both the maleimide-activated poly HRP/secondary antibody sample and the Traut's Reagent activated polyHRP were injected into 3-12 ml Slide-A-Lyzers® and dialyzed against 50 mM borate buffer at pH 8 for two hours. The samples were removed from the Slide-A-Lyzers® and 5 M sodium cyanoborohydride, prepared in 10 mM NaOH, was added and both samples were incubated for one hour. Quenching buffer, 3 M ethanolamine, was added to both samples and the samples were incubated for 15 minutes. The samples were then diluted 1:50 in 10 mM PBS and scanned from $\lambda_{500}$-$\lambda_{250}$.

The maleimide-activated poly HRP/secondary antibody and the Traut's Reagent activated polyHRP were combined so that amounts which produced equal OD at $\lambda_{420}$ were mixed for each sample. The combined sample was dialyzed against two changes of 10 mM PBS. The unreacted sulfhydryls were quenched in the sample with 10 μl/ml N-ethyl maleimide (NEM), at 0.3 M in DMF, and incubated at RT for 15 minutes.

The sample was purified using a Superdex 200 FPLC column and fractions from the first peak were pooled. The sample was scanned from $\lambda_{500}$ to $\lambda_{250}$ to determine the protein concentration and to evaluate the HRP to secondary antibody ratio. The conjugate was diluted to 1 mg/ml with respect to protein concentration.

EXAMPLE 18

Figure 22:
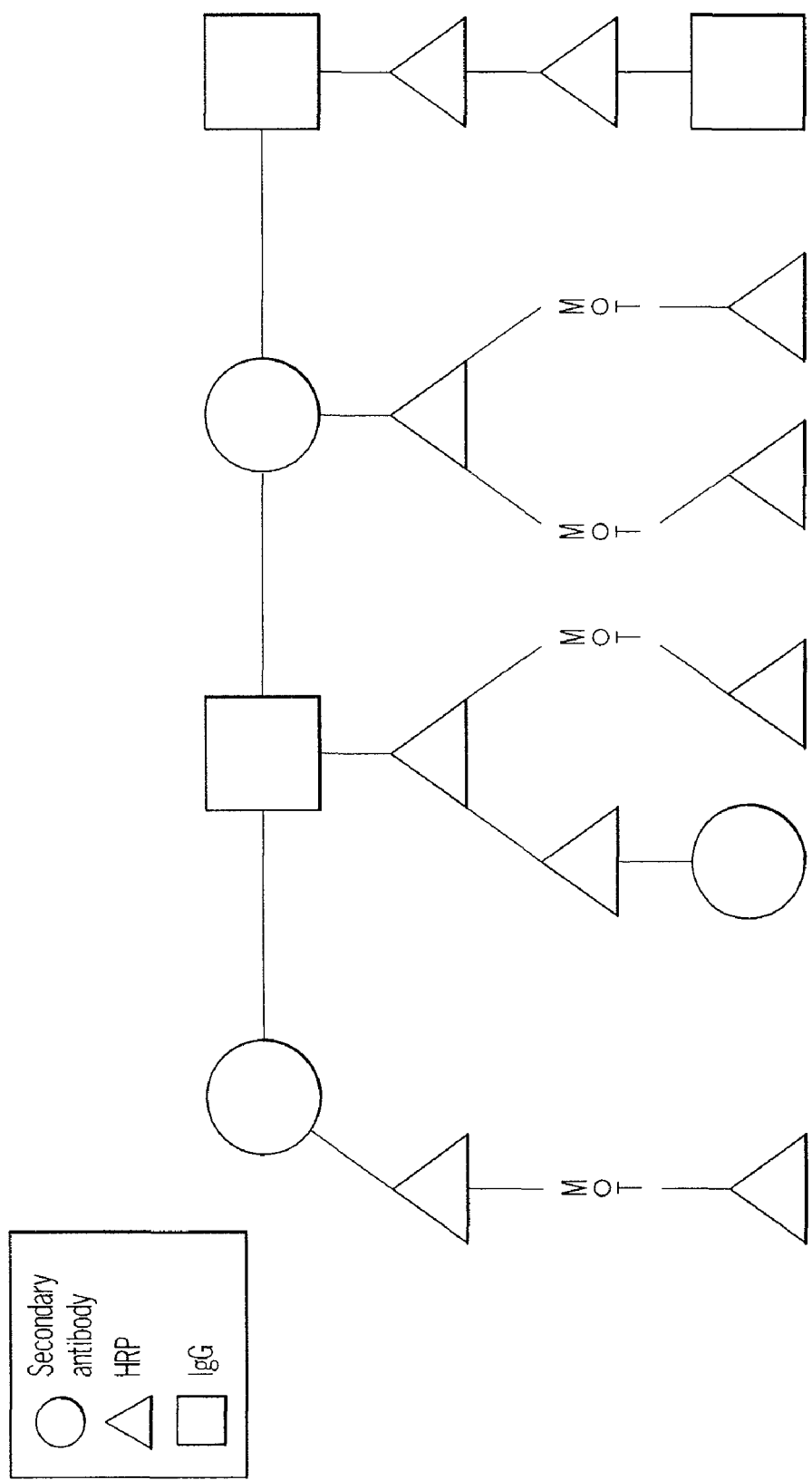
FIG. 22 is a schematic representation of a polymerized conjugate in one embodiment.

Preparation of secondary antibody-non specific IgG poly-HRP, as shown schematically in FIG. 22, at a ratio of 3.3 mg of HRP/1 mg of secondary antibody was prepared. Secondary antibody, non-specific IgG, and HRP were reconstituted at 10 mg/ml, 10 mg/ml, and 50 mg/ml, respectively, in 10 mM PBS. HRP was dialyzed against two changes of 10 mM sodium phosphate buffer, pH 7.2. The protein concentrations of secondary antibody, non-specific IgG, and HRP were determined by diluting each sample 1:50 and determining $\lambda_{280}$. A 0.5 molar excess of sulfo-SMCC, dissolved in DMSO at 10 mg/ml, was added to half the amount of the dialyzed HRP and allowed to react for 20 minutes. A 75 molar excess of sodium meta-periodate, dissolved in ultrapure water at 100 mg/ml, was added and allowed to react for 10 minutes. The required amounts of secondary antibody and non-specific IgG were then added at a 1:1 ratio.

To the remaining dialyzed HRP, a six molar excess of Traut's Reagent dissolved in ultrapure water at 10 mg/ml was added to achieve a ratio of 2.2 mg HRP:1 mg secondary antibody, and allowed to react for 20 minutes. A 75 molar excess of sodium meta-periodate, dissolved in ultrapure water at 100 mg/ml, was then added and allowed to react for 10 minutes.

Both the maleimide-activated poly HRP/BSA/streptavidin sample and the Traut's Reagent activated polyHRP were injected into 3-12 ml Slide-A-Lyzers® and dialyzed against 50 mM borate buffer at pH 8 for two hours. The samples were removed from the Slide-A-Lyzers® and 5 M sodium cyanoborohydride, prepared in 10 mM NaOH, was added and both samples were incubated for one hour. Quenching buffer, 3 M ethanolamine, was added to both samples and the samples were incubated for 15 minutes. The samples were then diluted 1:50 in 10 mM PBS and scanned from $\lambda_{500}$-$\lambda_{250}$.

The maleimide-activated poly HRP/non-specific IgG/secondary antibody and the Traut's Reagent activated polyHRP were combined so that amounts which produced equal OD at $\lambda_{420}$ were mixed for each sample. The combined sample was dialyzed against two changes of 10 mM PBS. The unreacted sulfhydryls were quenched in the sample with 10 μl/ml N-ethyl maleimide (NEM), at 0.3 M in DMF, and incubated at RT for 15 minutes.

The sample was purified using a Superdex 200 FPLC column and fractions from the first peak were pooled. The sample was scanned from $\lambda_{500}$ to $\lambda_{250}$ to determine the protein concentration and to evaluate the HRP to antibody ratio. The conjugate was diluted to 1 mg/ml with respect to protein concentration.

Other variations or embodiments will also be apparent to one of ordinary skill in the art from the above figures, description, and examples. For example, in the polyHRP/streptavidin conjugate, a HRP molar excess of 1× and 2× may also be used. Thus, the foregoing embodiments are not to be construed as construed as limiting the scope of the following claims.

What is claimed is:

1. A polymerized indicator-binding compound complex composition comprising
   a first polymer indirectly linked to a second polymer, where the first polymer comprises at least a first indicator molecule directly linked to a second indicator molecule and at least one binding compound directly linked to at least one indicator molecule, and where the second polymer comprises at least a third indicator molecule directly linked to a fourth indicator molecule, and where at least one indicator molecule of the first polymer is indirectly linked to an indicator molecule of the second polymer, wherein directly linked molecules comprise covalent bonds between the molecules, and indirectly linked molecules comprise covalent bonds between the molecules and a linker moiety, and
   at least one biocompatible excipient,
   wherein the composition is a polymerized indicator-binding compound complex.

2. The composition of claim 1 wherein the binding compound is selected from the group consisting of streptavidin, deglycosylated avidin, avidin, biotin, lectins, Protein A, Protein G, glycoproteins, peptides, hormones, receptors, antigens, drugs, antibodies and portions thereof, antigen binding fragments, RNA, DNA, oligonucleotides, and combinations thereof.

3. The composition of claim 1 wherein the indicator is a peroxidase or a phosphatase.

4. The composition of claim 3 wherein the peroxidase is horseradish peroxidase or the phosphatase is alkaline phosphatase.

5. The composition of claim 1 where the linker moiety comprises a maleimide-containing group.

6. The composition of claim 1 where the directly linked molecules comprise covalent bonds formed between an amine group on one molecule and an oxidized carbohydrate group on another molecule.

7. A method of forming a polymerized indicator-binding compound complex, the method comprising
   (a) forming a polymerized, activated indicator-binding compound composition by reacting an indicator with at least a first activation agent under conditions to result in an activated indicator, and thereafter adding a binding compound to the activated indicator, under conditions to result in a polymerized, activated indicator-binding compound composition,
   (b) separately reacting an indicator with at least a second activation agent under conditions to result in a polymerized, activated indicator compound,
   (c) thereafter reacting the polymerized, activated indicator-binding compound composition from step (a) with the polymerized, activated indicator compound from step (b) under conditions to form a polymerized indicator-binding compound complex, wherein the polymerized indicator-binding compound complex comprises at least one indicator directly linked with another indicator, and at least one indicator directly linked with a binding compound.

8. The method of claim 7 wherein the first activation agent is sulfosuccinimidyl 4-(N-maleimidomethyl)cyclo-hexane-1-carboxylate (sulfo-SMCC), and the second activation agent is 2-iminothiolane.

9. The method of claim 7 wherein the indicator is a peroxidase or a phosphatase.

10. The method of claim 9 wherein the peroxidase is horseradish peroxidase or the phosphatase is alkaline phosphatase.

11. The method of claim 7 wherein the binding compound is selected from the group consisting of streptavidin, deglycosylated avidin, avidin, biotin, lectins, Protein A, Protein G, glycoproteins, peptides, hormones, receptors, antigens, drugs, antibodies and portions thereof, antigen binding fragments, RNA, DNA, oligonucleotides, and combinations thereof.

12. The method of claim 7 further comprising adding an oxidizing agent to the indicator of step (a) and/or step (b).

13. The method of claim 12 where in step (a), the oxidizing agent is added prior to the addition of the binding compound.

14. The method of claim 12 where the oxidizing agent is a periodate.

15. A kit comprising
    a polymerized indicator-binding compound complex composition comprising a first polymer indirectly linked to a second polymer, where the first polymer comprises at least a first indicator molecule directly linked to a second indicator molecule and at least one binding compound directly linked to at least one indicator molecule, and where the second polymer comprises at least a third indicator molecule directly linked to a fourth indicator molecule, and where at least one indicator molecule of the first polymer is indirectly linked to an indicator molecule of the second polymer, wherein directly linked molecules comprise covalent bonds between the molecules, and indirectly linked molecules comprise covalent bonds between the molecules and a linker moiety, and
    instructions for using the polymerized indicator conjugate composition.

* * * * *